United States Patent [19]

Wiersdorff et al.

[11] 4,335,138

[45] Jun. 15, 1982

[54] NOVEL CARBAMATES, THEIR PREPARATION, AND PHARMACEUTICAL FORMULATIONS CONTAINING THESE COMPOUNDS

[75] Inventors: Walter-Wielant Wiersdorff, Mutterstadt; Karl-Heinz Geiss, Beindersheim; Harald Weifenbach, Ludwigshafen; Wolfgang Worstmann, Gruenstadt; Dieter Lenke, Ludwigshafen; Rolf Kretzschmar, Gruenstadt, all of Fed. Rep. of Germany

[73] Assignee: BASF Aktiengesellschaft, Fed. Rep. of Germany

[21] Appl. No.: 186,841

[22] Filed: Sep. 15, 1980

[30] Foreign Application Priority Data

Sep. 29, 1979 [DE] Fed. Rep. of Germany ....... 2939660

[51] Int. Cl.$^3$ ............... C07C 125/065; C07C 125/04; C07D 339/08; C07D 339/06; C07D 333/36; C07D 307/66; A01N 47/12; A01N 47/20

[52] U.S. Cl. ..................... 424/275; 549/371; 549/373; 260/463; 568/345; 568/374; 260/464; 568/376; 568/377; 424/276; 549/378; 549/419; 424/277; 549/449; 549/452; 424/278; 549/478; 549/480; 424/283; 549/493; 549/496; 424/285; 424/299; 424/300; 560/27; 560/29; 560/31; 560/32; 560/115; 560/148; 560/160; 560/161; 560/162; 549/13; 549/14; 549/21; 549/22; 549/28; 549/30; 549/38; 549/39; 549/63; 549/65; 549/69; 549/76; 549/77; 549/330

[58] Field of Search .......... 260/340.6, 340.7, 340.9 R, 260/345.8 R, 347.4, 464; 560/27, 29, 31, 32, 115, 148, 160, 161, 162; 549/13, 14, 21, 22, 28, 30, 38, 39, 69, 65, 20, 76, 77, 63; 424/275, 276, 277, 278, 283, 285, 300, 299

[56] References Cited

U.S. PATENT DOCUMENTS 3,418,362 12/1968 Goonewardene .................. 560/162
3,965,119 6/1976 Amann ........................ 260/343.3 R

FOREIGN PATENT DOCUMENTS 1122937 of 0000 Fed. Rep. of Germany .
855210 11/1960 United Kingdom ................ 560/162
929350 6/1963 United Kingdom ................ 560/162

*Primary Examiner*—Michael L. Shippen
*Attorney, Agent, or Firm*—Keil & Witherspoon

[57] ABSTRACT

Novel carbamates derived from substituted cyclic β-keto-alcohols, their preparation, and pharmaceutical formulations which contain these compounds and which may be used as hypnotics in the treatment of sleep disturbance and as sedatives.

15 Claims, No Drawings

NOVEL CARBAMATES, THEIR PREPARATION, AND PHARMACEUTICAL FORMULATIONS CONTAINING THESE COMPOUNDS

The present invention relates to novel carbamates derived from substituted cyclic β-keto-alcohols, to their preparation and to pharmaceutical formulations which contain these compounds and which may be used as hypnotics in the treatment of sleep disturbances and as sedatives.

The prior art hypnotics exhibit more or less pronounced side-effects (D. Ginestet et al., Therapie 31 (1976), 77–103).

Further, it is known, for example from German Laid-Open Application DOS No. 2,346,305, that carbamates derived from tricyclic γ-hydroxylactones, for example 4-oxa-5-(5-methylcarbamyloxy)-tricyclo[5,2,1,0$^{2,6}$]-dec-8-en-3-one exhibit analgesic properties.

It is an object of the present invention to provide novel and advantageous hypnotics.

We have found that compounds of the general formula I

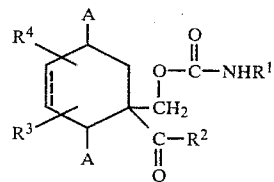

(I)

where the broken line is a double bond which may or may not be hydrogenated and the radicals A are each hydrogen, or the two radicals A together are a bridge, joining the two carbon atoms, of the formula —(CH$_2$)$_m$—, where m is an integer from 1 to 3, and which may or may not be substituted by 1, 2 or 3 lower alkyl, or a bridge of the formula

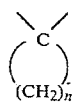

where n is an integer from 2 to 4, and R$^1$ is hydrogen, or is a saturated straight-chain or branched alkyl radical of 1 to 12 carbon atoms, which is unsubstituted, or is monosubstituted, disubstituted or trisubstituted by halogen, lower alkoxy or lower alkylthio, or is monosubstituted by cyano or by cycloalkyl of 3 to 6 carbon atoms in the ring, which ring is unsubstituted or substituted by 1, 2 or 3 lower alkyl and may, in the case of a 5-membered or 6-membered ring, have 1 or 2 carbon atoms replaced by oxygen or sulfur, or by bicycloalkyl of 5 to 8 carbon atoms in the bicyclic system, which is unsubstituted or substituted by 1, 2 or 3 lower alkyl, or is monosubstituted or disubstituted by phenyl, furyl or thienyl, which are unsubstituted or substituted by halogen, lower alkyl or lower alkoxy, or is alkenyl or alkynyl of 2 to 12 carbon atoms, alkenyl being unsubstituted or substituted by 1, 2 or 3 chlorine atoms, or is cycloalkyl of 3 to 7 carbon atoms in the ring, which ring is unsubstituted or substituted by 1, 2, 3 or 4 lower alkyl or by phenyl and may, in the case of a 5-membered or 6-membered ring, have 1 or 2 carbon atoms replaced by oxygen or sulfur, or is bicycloalkyl of 5 to 8 carbon atoms in the bicyclic system, which is saturated or unsaturated and is unsubstituted or substituted by 1, 2 or 3 lower alkyl, or is phenyl, furyl or thienyl, which is unsubstituted or monosubstituted or disubstituted by halogen, lower alkyl or lower alkoxy, R$^2$ is saturated straight-chain or branched alkyl of 1 to 6 carbon atoms and R$^3$ and R$^4$ independently of one another are each hydrogen or lower alkyl, have valuable pharmacological properties.

For the purposes of the invention, lower alkyl, lower alkoxy and lower alkylthio is in each case a radical of 1 to 4 carbon atoms which may, in the case of 3 or 4 carbon atoms, be straight-chain or branched.

The compounds of the general formula I in which the two radicals A together form a bridge may exist as exo- and endo-compounds, the terms exo and endo relating to the relative position of the group

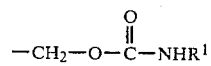

on the six-membered ring bridged by the groups A,A. The structure is allotted by NMR-spectroscopic comparison of the

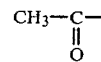

signals with those of exo- and endo-norbornenyl methyl ketone, or by X-ray structural analysis.

The following are specific examples of possible meanings of the radicals mentioned:

Examples of carbon bridges of the formula —(CH$_2$)$_m$— and

are methylidene, 1,1-ethylidene, 1,2-ethylidene, 1,3-propylidene, 2,3-butylidene, 1,1-cyclopropylidene, 1,1-cyclobutylidene and 1,1-cyclopentylidene.

Examples of straight-chain or branched alkyl, alkenyl and alkynyl R$^1$ are methyl, ethyl, n- and i-propyl, n-, i-, sec.- and tert.-butyl, n-pentyl, pent-3-yl, 3-methyl-but-2-yl, n-hexyl, n-octyl, 2-ethyl-hex-1-yl, ethenyl, prop-1-enyl, prop-1-en-2yl, 2-methylprop-1-en-1-yl, hex-1-enyl, allyl, methallyl, but-3-en-1-yl, but-3-en-2-yl, hex-5-en-2-yl, prop-2ynyl, but-2-ynyl, but-1-yn-3-yl and 2-methylbut-3-yn-2-yl.

Examples of substituted alkyl R$^1$ are: 2-fluoroethyl, 2-chloroethyl, 2,2,2-trifluoroethyl, 3-chloro-prop-1-yl, 3-bromo-prop-1-yl, 1-chloro-prop-2-yl, 1,3-difluoro-prop-2-yl, 2-chloroethenyl, 2,2-dichloroethenyl, cyanomethyl, 1-cyanoethyl, 2-cyanoethyl, 1-cyano-prop-2-yl, 1-cyano-hex-3-yl, methoxymethyl, ethoxymethyl, isopropoxymethyl, 1-ethoxyethyl, 3-isopropoxypropyl, 1-methoxy-prop-2-yl, 1,1-dimethoxy-prop-2-yl, 1,1-diethoxy-prop-3-yl, 1,5-dimethoxy-pent-3-yl, methylthiomethyl, isopropylthiomethyl, 2-methylthioethyl, 1-methylthioethyl, 1-isopropylthio-prop-2-yl, 3,3-bismethylthiopropyl, cyclopropylmethyl, 2,2-dimethylcyclopropylmethyl, 1-cyclopropylethyl, 2-cyclopropylethyl, 1-cyclopropyl-prop-2-yl, cyclobutylmethyl, 1-cyclobutylethyl, cyclopentylmethyl, cyclohexyl-methyl, (2-tetrahydrofuryl)-methyl, 1-(3-tetrahydrofuryl)-ethyl, (2,5-dimethyl-3-tetrahydrofuryl)-methyl, 2-(2-tetrahydrothienyl)-ethyl, (4-methyl-tetrahydropyran-3-yl)-methyl, (1,3-dioxolan-2-yl)-ethyl, 2-(1,3-dioxolan-2-yl)-ethyl, 2-(1,3-dioxolan-2-yl)-prop-1-yl, 2-methyl-1-(4-methyl-1,3-dioxolan-2-yl)-propyl, (1,3-dithian-2-yl)-methyl, (bicyclo-[3.1.0]-hex-6-yl)-methyl, norborn-5-en-2-ylmethyl, (2,7,7-trimethylbicyclo-[3.1.1]-heptyl)-methyl, benzyl, p-chlorobenzyl, 3,4-dimethoxyphenethyl, 2-phenylpropyl, 3,3-diphenylpropyl, 2-furylmethyl and 2,3-dibromothien-4-ylmethyl.

Examples of cycloalkyl $R^1$ are: cyclopropyl, 1-methylcyclopropyl, 2-methylcyclopropyl, 2,2-dimethylcyclopropyl, 2-phenylcyclopropyl, 2-(2-propyl)-cyclopropyl, cyclobutyl, cyclopentyl, cyclohexyl, 3,3,5-trimethylcyclohexyl, cycloheptyl, tetrahydrofur-2-yl, tetrahydrofur-3-yl, tetrahydrothien-2-yl, 2-isopropyl-4-methyltetrahydropyran-4-yl and 2-methyl-1,3-dithian-5-yl.

Examples of bicyclic alkyl $R^1$ are bicyclo-[3.1.0]-hex-6-yl, bicyclo-[3.1.0]-hex-3-yl, norborn-5-en-2-yl, bicyclo-[2.2.2]-oct-2-yl and 7,7-dimethylbicyclo-[3.1.1]-hept-2-yl.

Examples of phenyl, furyl or thienyl which are unsubstituted or substituted by halogen, lower alkyl or lower alkoxy are p-chlorophenyl, 3,4-dichlorophenyl, p-methoxyphenyl, 3-methyl-4-methoxy-phenyl, p-isopropylphenyl, fur-2-yl, fur-3-yl, thien-2-yl, thien-3-yl and 3-bromofur-5-yl.

Examples of radicals $R^2$ are methyl, ethyl, n-propyl, isopropyl, n-butyl, but-2-yl, isobutyl, tert.-butyl, n-pentyl, pent-3-yl, n-hexyl and hex-2-yl.

Examples of radicals $R^3$ and $R^4$ are hydrogen, methyl, ethyl, n- and i-propyl and n-, sec-, i- and tert.-butyl.

In the preferred compounds of the formula I, where the broken line is a double bond, which may or may not be hydrogenated, the radicals A are hydrogen or together form a bridge of the formula $-(CH_2)_m-$, where m is 1 or 2, and $R^1$ is saturated straight-chain or branched alkyl of 1 to 6 carbon atoms, which is unsubstituted, or is monosubstituted, disubstituted or trisubstituted by halogen, especially fluorine, chlorine or bromine, or is monosubstituted by lower alkoxy, by cyano, by lower alkylthio, by cycloalkyl of 3 to 6 carbon atoms in the ring, which is unsubstituted or substituted by lower alkyl and, in the case of a 5-membered or 6-membered ring, may contain an oxygen or a sulfur in place of 1 carbon atom or of 2 non-adjacent carbon atoms, or by furyl, or is alkenyl or alkynyl of 2 to 6 carbon atoms, alkenyl being unsubstituted or substituted by 1, 2 or 3 chlorine atoms, or is cycloalkyl of 3 to 6 carbon atoms in the ring, which is unsubstituted or substituted by 1, 2 or 3 lower alkyl, preferably methyl or ethyl, $R^2$ is methyl or ethyl and $R^3$ and $R^4$ are each hydrogen or methyl.

Particularly preferred compounds of the formula I are those where the broken line is a double bond, which may or may not be hydrogenated, and the radicals A are each hydrogen or together are methylene ($-CH_2-$) and $R^1$ is saturated, straight-chain or branch unsubstituted alkyl of 1 to 6 carbon atoms, or alkyl of 1 to 3 carbon atoms which is substituted by chlorine, by lower alkoxy of preferably 1 to 3 carbon atoms, especially by methoxy, or by cycloalkyl of 3 or 4 carbon atoms in the ring, or is alkenyl or alkynyl of 2 to 6 carbon atoms or is cycloalkyl of 3 to 5 carbon atoms in the ring, $R^2$ is methyl and $R^3$ and $R^4$ are each hydrogen.

The following are examples of compounds according to the invention: others will be found in the Examples illustrating the process of preparation: 2-[N-(2-fluoropropyl)-carbamyloxymethyl]-norborn-5-en-2-yl methyl ketone, 2-[N-(3-fluoropropyl)-carbamyloxymethyl]-norborn-5-en-2-yl methyl ketone, 2-[N-(1-chloro-prop-2-yl)-carbamyloxymethyl]-norborn-5-en-2-yl methyl ketone, 2-[N-(prop-1-en-2-yl)-carbamyloxymethyl]-norborn-5-en-2-yl methyl ketone, 2-N-[1-(2-methylcyclopropyl)-ethyl]-carbamyloxymethyl-norborn-5-en-2-yl methyl ketone, 2-[N-(1-cyclobutylethyl)-carbamyloxymethyl]-norborn-5-en-2-yl methyl ketone, 2-[N-(1-cyclopentylethyl)-carbamyloxymethyl]-norborn-5-en-2-yl methyl ketone, 2-[N-(2-methylcyclopropyl)-carbamyloxymethyl]-norborn-5-en-2-yl methyl ketone, 2-(N-cyclopent-2-enylcarbamyloxymethyl)-norborn-5-en-2-yl methyl ketone, 2-(N-but-1-en-3-ylcarbamyloxymethyl)-norborn-5-en-2-yl methyl ketone, 2-(N-but-2-en-1-ylcarbamyloxymethyl)-norborn-5-en-2-yl methyl ketone, 2-(N-but-3-en-1-ylcarbamyloxymethyl)-norborn-5-en-2-yl methyl ketone, 2-(N-ethylcarbamyloxymethyl)-7,7-dimethylnorborn-5-en-2-yl methyl ketone, 2-(N-isopropylcarbamyloxymethyl)-7,7-dimethylnorborn-5-en-2-yl methyl ketone, 2-(N-isopropylcarbamyloxymethyl)-3-methylnorborn-5-en-2-yl methyl ketone, 2-(N-ethylcarbamyloxymethyl)-3-methylnorborn-5-en-2-yl methyl ketone, 2-(N-ethylcarbamyloxymethyl)-5,6-dimethylnorborn-5-en-2-yl methyl ketone, 2-(N-isopropylcarbamyloxymethyl)-5,6-dimethylnorborn-5-en-2-yl methyl ketone, 2-(N-cyclopropylcarbamyloxymethyl)-5,6-dimethylnorborn-5-en-2-yl methyl ketone, 2-(N-cyclopropylcarbamyloxymethyl)-norborn-5-en-2-yl ethyl ketone, 2-[N-(1-cyclopropylethyl)-carbamyloxymethyl]-norborn-5-en-2-yl ethyl ketone, 2-(N-cyclopropylcarbamyloxymethyl)-norborn-2-yl methyl ketone, 2-[N-(1-cyclopropylethyl)-carbamyloxymethyl]-norborn-2-yl methyl ketone, 2-(N-prop-1-en-2-ylcarbamyloxymethyl)-bicyclo-[2.2.2]-oct-5-en-2-yl methyl ketone, 2-(N-cyclopropylcarbamyloxymethyl)-bicyclo-[2.2.2]-oct-5-en-2-yl methyl ketone, 1-(N-3-chloropropylcarbamyloxymethyl)-cyclohex-3-enyl methyl ketone, 1-(N-2-chloroethylcarbamyloxymethyl)-cyclohex-3-enyl methyl ketone, 1-(N-cyclopropylmethylcarbamyloxymethyl)-cyclohex-3-enyl methyl ketone, 1-[N-(1-cyclobutylethyl)-carbamyloxymethyl]-cyclohex-3-enyl methyl ketone; 1-(N-cyclopentylmethylcarbamyloxymethyl)-cyclohex-3-enyl methyl ketone, 1-(N-but-3-enylcarbamyloxymethyl)-cyclohex-3-enyl methyl ketone, 1-(N-but-1-en-3-yl-carbamyloxymethyl)-cyclohex-3-enyl methyl ketone, 1-(N-but-2-en-1-ylcarbamyloxymethyl)-cyclohex-3-enyl methyl ketone, 1-(N-allylcarbamyloxymethyl)-cyclohex-3-enyl methyl ketone, 1-(N-n-propylcarbamyloxymethyl)-4-methylcyclohex-3-enyl methyl ketone, 1-(N-isopropylcarbamyloxymethyl)-4-methylcyclohex-3-enyl methyl ketone, 1-(N-cyclopropylcarbamyloxymethyl)-4-methylcyclohex-3-enyl methyl ketone, 1-[N-(1-cyclopropylethyl)-carbamyloxymethyl]-4-methylcyclohex-3-enyl methyl ketone, 1-(N-cyclopropylcarbamyloxymethyl)-cyclohexyl methyl ketone, 1-[N-(1-cyclopropylethyl)-carbamyloxymethyl]-cyclohexyl methyl ketone and 1-(N-propylcarbamyloxymethyl)-cyclohexyl methyl ketone.

The novel compounds of the formula I may be prepared as follows:
(a) by reaction of a β-keto-alcohol of the general formula II

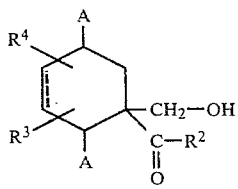

(II)

where the broken line is a double bond, which may or may not be hydrogenated, and the radicals A, $R^2$, $R^3$ and $R^4$ have the meanings given for formula I, with an isocyanate of the general formula III $$R^1 + N=C=O \quad \text{(III)}$$

where $R^1$ has the meanings given for formula I, or with an acid adduct thereof in the presence of a base, advantageously in an inert solvent, in the presence or absence of a catalyst, with or without subsequent catalytic hydrogenation if the compound obtained is unsaturated; or (b) by reaction of a β-keto-alcohol of the general formula II, in the form of a carbonic acid ester of the formula IV

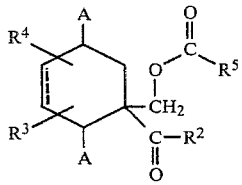

(IV)

where A, $R^2$, $R^3$ and $R^4$ have the meanings given for formula I and $R^5$ is halogen, preferably chlorine, or is —OAr, Ar being unsubstituted or substituted phenyl, with an amine of the general formula V $$R^1\text{-NH}_2 \quad \text{(V)}$$

where $R^1$ has the meanings given for formula I, with the proviso that $R^1$ does not contain a double or triple bond in the α,β-position relative to the nitrogen, advantageously in a solvent, in the presence or absence of a basic catalyst, with or without subsequent catalytic hydrogenation if the compound obtained is unsaturated.

Hydrogenation, in a conventional manner, of a double bond which may be present in the ring of a compound of the formula I is only advisable if the substituents present are inert under the hydrogenation conditions.

The reaction of a compound of the general formula II with an isocyanate of the formula III may be carried out in the presence or absence of an inert solvent. Advantageously, an organic aprotic solvent is used, such as a lower saturated dialkyl ether, dialkyl glycol ether or saturated cyclic ether, eg. diethyl ether, methyl tert.-butyl ether, 1,2-dimethoxyethane, tetrahydrofuran or dioxane, an aromatic hydrocarbon, such as benzene or an alkylbenzene, eg. toluene or xylene, an aliphatic hydrocarbon, eg. hexane, cyclohexane, heptane or octane, a lower aliphatic ketone, eg. acetone, methyl ethyl ketone or methylisobutyl ketone, a lower chlorinated hydrocarbon, eg. methylene chloride or chloroform, a dialkylformamide, eg. dimethylformamide, or diethylformamide, or an N-alkyl-lactam, eg. N-methylpyrrolidone. The reaction may also be carried out in mixtures of the above solvents.

The reactions are as a rule carried out at from 0° to 140° C., preferably from 20° to 100° C.

Advantageously, the reactions are carried out under atmospheric pressure, but they may also be carried out in a closed vessel under superatmospheric pressure.

The reaction of a compound of the general formula II with an isocyanate $R^1$NCO can advantageously be carried out in the presence of a catalyst. Examples of catalysts include, as is known to those skilled in the art, lead(IV), tin(II), tin(IV) and mercury(II) compounds, and tertiary amines (cf., for example, J. Appl. Polym. Sci., 13 (1969), 1929 et seq.; Chem. Rev. 72 (1972), 457 et seq.). Preferred catalysts are tin(II), tin(IV) and mercury(II) compounds, eg. tin octanoate, dibutyl-tin diacetate and phenyl-mercury acetate.

Preferred solvents for reactions carried out in the presence of a catalyst, the latter being present, as a rule, in an amount of from 0.1 to 2% by weight, based on keto-alcohol of the formula II, are lower saturated dialkyl ethers, dialkyl glycol ethers and cyclic ethers, eg. diethyl ether, 1,2-dimethoxyethane and tetrahydrofuran.

Where $R^1$ is hydrogen, it is advantageous to produce the required cyanic acid in a separate vessel and to introduce it, as a gas, into the solution of the keto-alcohol of the formula II, or to react the cyanic acid in situ to give the desired compound of the formula I, where $R^1$ is H.

Advantageously, the cyanic acid is produced in situ from an alkali metal cyanate, eg. sodium cyanate or potassium cyanate, and a strong acid, eg. sulfuric acid or trifluoroacetic acid, in a conventional manner (cf., for example, B. Loev and M. F. Kormendy, J. Org. Chem. 28 (1963), 3421) and reacted with a keto-alcohol of the formula II present in the same solution. This reaction can also be carried out with or without an added solvent; examples of suitable solvents include benzene and alkylbenzenes, eg. toluene and xylene, lower saturated dialkyl ethers and cyclic ethers, eg. diethyl ether and tetrahydrofuran, and lower chlorohydrocarbons, eg. methylene chloride. The reaction is carried out at from 0° to 80° C., preferably from 10° to 60° C.

Compounds according to the invention, of the formula I, where $R^1$ is hydrogen, may also be prepared by a two-stage synthesis from a keto-alcohol of the formula II by reacting the latter with a suitable isocyanate, eg. chlorosulfonyl isocyanate, 1-tetrahydropyranyl isocyanate or trimethylsilyl isocyanate, and then hydrolyzing the carbamate obtained.

It is to be noted that in place of the isocyanate $R^1$NCO, its adduct with an acid, ie. the carbamic acid chloride $R^1$-NHCOCl, may be used for the reaction with the keto-alcohol of the general formula II, the reaction then advantageously being carried out in an inert solvent in the presence of an acid acceptor, preferably an organic tertiary amine, eg. triethylamine, N-methylpiperidine, N-methylpyrrolidone or N,N-dimethylaniline.

Furthermore, it is possible to obtain a compound according to the invention, of the formula I, by transesterification of a carbamate of the formula $R^1$NHCOOR$^6$, where $R^1$ has the above meanings and $R^6$ is lower alkyl or phenyl, which is unsubstituted or substituted, with a keto-alcohol of the general formula II.

The reaction of a compound of the general formula IV with an amine of the general formula V may be carried out in the presence or absence of a solvent; the amine R¹NH₂, which may or may not be used in excess, can itself serve as the solvent. The amine may also be employed in the form of an addition salt with an acid, especially in the form of a hydrohalide, in the presence of a base, for example in the presence of the equivalent amount of sodium methylate.

$R^5$ is halogen or phenoxy which is unsubstituted or substituted by 1 or 2 electronegative radicals, especially by halogen or nitro; preferably, $R^5$ is chlorine or phenoxy.

The reaction is carried out at from 0° to 120° C., preferably from 20° to 80° C.

Suitable solvents for this reaction include water, lower alcohols of 1 to 4 carbon atoms, eg. methanol, ethanol, isopropanol and isobutanol, lower saturated dialkyl ethers, dialkyl glycol ethers and cyclic ethers, eg. diethyl ether, methyl tert.-butyl ether, 1,2-dimethoxyethane, tetrahydrofuran and dioxane, aromatic hydrocarbons, such as benzene and alkylbenzenes, eg. toluene and xylene, aliphatic hydrocarbons, eg. hexane, heptane and cyclohexane, dialkylformamides, eg. dimethylformamide and diethylformamide, and chlorohydrocarbons, eg. methylene chloride and chloroform. Mixtures of these solvents may also be employed. Preferred solvents include the lower saturated dialkyl ethers, dialkyl glycol ethers and cyclic ethers, eg. diethyl ether, methyl tert.-butyl ether, 1,2-dimethoxymethane, tetrahydrofuran and dioxane.

The phenol formed in the reaction can be removed by recrystallizing the novel compound of the formula I after distilling off the solvent, or by extracting the reaction solution with an alkali metal hydroxide solution, eg. sodium hydroxide solution, if appropriate after having replaced the reaction solvent by a solvent which is not completely miscible with water, or by column chromatography of the crude product. The novel compound can then be purified further by distillation and/or recrystallization and/or column chromatography.

An advantageous method of hydrogenating a double bond present in the ring is to dissolve or suspend the corresponding unsaturated carbamate of the general formula I in a solvent which is inert under the hydrogenation conditions and to carry out the hydrogenation with hydrogen in the presence of a catalyst. Suitable hydrogenation catalysts include transition metals, eg. palladium, platinum or nickel, which may or may not be supported on a carrier, eg. charcoal, $CaCO_3$ or silica gel. Suitable solvents include lower aliphatic alcohols, eg. methanol, ethanol, isopropanol and isobutanol, lower saturated dialkyl ethers, dialkyl glycol ethers and cyclic ethers, eg. diethyl ether, 1,2-dimethoxyethane and tetrahydrofuran, and lower alkyl esters of lower aliphatic carboxylic acids, eg. methyl acetate and ethyl acetate. The reaction may be carried out under atmospheric pressure or in a closed vessel under superatmospheric pressure, of up to 250 bar, at room temperature or with heating, for example at 30°–150° C. Preferably, the hydrogenation is carried out at 20°–60° C.

The starting compounds of the general formula II may be obtained in a conventional manner by reacting a ketone of the general formula VI

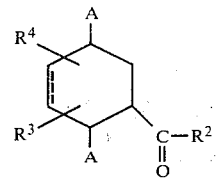

where $R^2$, $R^3$, $R^4$, A and B have the meanings given in formula I, and the broken line is a double bond which may or may not be hydrogenated, with formaldehyde in the presence of a basic catalyst.

Keto-alcohols of the formula II, wherein the two radicals A form a bridge, are in general obtained as exo/endo mixtures, from which the pure isomers can, if desired, be obtained by recrystallization or column chromatography.

A double bond present in the ring of a compound of the formula II may, if desired, be hydrogenated catalytically in a conventional manner.

The starting compounds of the formula IV may be obtained by reacting a compound of the formula II with a carbonic acid derivative of the general formula VII

where $R^5$ is halogen, preferably chlorine, or OAr, L is halogen, preferably chlorine or, if $R^5$ is OAr, has the same meaning as $R^5$, and Ar is unsubstituted or substituted phenyl. The reaction is advantageously carried out in the presence of a basic catalyst, eg. a tertiary amine. In a preferred embodiment, the starting material used is a diaryl carbonate of the formula VII, ie. L is OAr.

A double bond present in the ring of a compound of the formula IV may, if desired, also be catalytically hydrogenated in a conventional manner.

The substances according to the invention exhibit valuable pharmacological properties. They have a wide therapeutic range together with a high hypnotic activity and can accordingly be used as hypnotics in the treatment of sleep disturbances, and as sedatives. In contrast to the compounds of German Laid-Open Application DOS No. 2,346,305, they do not exhibit any analgesic properties.

To investigate the hypnotic action, these substances are administered intraperitoneally to groups of 4–8 female Sprague-Dawley rats each weighing 145–200 g. The period of absence of the righting reflex (ie. the duration of sleep) served as a criterion of the hypnotic action.

Linear relationships exist between the logarithms of the administered doses (mg/kg) and the logarithms of the period of sleep (min), from which relationships the dose which causes a 60 minute period of sleep is calculated, as the ED 60 min, by regression analysis.

The acute toxicity is determined on groups of 10 rats of the same strain as above, again for intraperitoneal administration.

The LD 50 is calculated, by Probit analysis, after a 6 hour period of observation.

The comparison substance used is the well known hypnotic Ethinamate (1-ethynyl-cyclohexyl carbamate).

TABLE 1

Hypnotic action and toxicity
(on intraperitoneal administration to rats)

| Compound No. | Hypnotic action | | Toxicity | |
|---|---|---|---|---|
| | ED 60 min mg/kg | R.A. (1) | LD 50 mg/kg | Therapeutic range (2) |
| 7 | 20.7 | 3.35 | 137 | 6.6 |
| 4 | 21.5 | 3.22 | 392 | 18.2 |
| 15 | 46.4 | 1.49 | 247 | 5.3 |
| 36 | 37.6 | 1.84 | 464 | 12.3 |
| 109 | 27.2 | 2.55 | 187 | 6.9 |
| 87 | 46.7 | 1.48 | 482 | 10.3 |
| 88 | 30.8 | 2.25 | 150 | 4.9 |
| 52 | 28.5 | 2.43 | 215 | 7.5 |
| 98 | 30.3 | 2.29 | ≧681 (3) | ≧22.5 |
| Ethinamate | 69.3 | 1.00 | 296 | 4.3 |

(1) R.A. = relative activity. Ethinamate = 1.00
(2) $\frac{LD\ 50}{ED\ 60\ min}$
(3) Mortality rate 0/10

It may be seen from Table 1 that the substances according to the invention have a high hypnotic activity. The effective doses for the compounds investigated in Table 1 are, for rats, from 20.7 mg/kg (Example 7) to 46.7 mg/kg (Example 87). The activity is from 1.5 to 3.4 times as high as that of Ethinamate (69.3 mg/kg).

The ratio of the lethal dose (LD 50) to the hypnotically effective dose (ED 60 min), ie. the therapeutic range, is, for these compounds, from 4.9 (Example 88) to >22.5 (Example 98). It is greater than in the case of Ethinamate (4.3).

Specific examples of compounds to be mentioned because of their activity include: exo-2-(N-isopropylcarbamyloxymethyl)-norborn-5-en-2-yl methyl ketone, exo-2-(N-n-propylcarbamyloxymethyl)-norborn-5-en-2-yl methyl ketone, exo-2-(N-cyclopentylcarbamyloxymethyl)-norborn-5-en-2-yl methyl ketone, exo-2-(N-isopropylcarbamyloxymethyl)-norborn-2-yl methyl ketone, exo-2-(N-cyclopropylcarbamyloxymethyl)-norborn-5-en-2-yl methyl ketone, exo-2-(N-(2-methylpropyl)-carbamyloxymethyl)-norborn-5-en-2-yl methyl ketone, exo-2-(N-but-2-yl-carbamyloxymethyl)-norborn-5-en-2-yl methyl ketone, 1-(N-propylcarbamyloxymethyl)-cyclohex-3-enyl methyl ketone and exo-2-[N-(1-cyclopropylethyl)-carbamyloxymethyl]-norborn-5-en-2-yl methyl ketone.

Further, the following may be mentioned as examples of compounds with similar activity: exo-2-(N-ethylcarbamyloxymethyl)-norborn-5-en-2-yl methyl ketone, exo-2-(N-n-butylcarbamyloxymethyl)-norborn-5-en-2-yl methyl ketone, exo-2-(N-n-hexylcarbamyloxymethyl)-norborn-5-en-2-yl methyl ketone, exo-2-(N-vinylcarbamyloxymethyl)-norborn-5-en-2-yl methyl ketone, exo-2-(N-prop-1-enylcarbamyloxymethyl)-norborn-5-en-2-yl methyl ketone, exo-2-(N-methoxymethylcarbamyloxymethyl)-norborn-5-en-2-yl methyl ketone, endo-2-(N-isopropylcarbamyloxymethyl)-norborn-5-en-2-yl methyl ketone, 2-(N-isopropylcarbamyloxymethyl)-norborn-5-en-2-yl ethyl ketone, exo-2-(N-ethylcarbamyloxymethyl)-norborn-2-yl methyl ketone, exo-2-(N-n-propylcarbamyloxymethyl)-norborn-2-yl methyl ketone, 1-(N-ethylcarbamyloxymethyl)-cyclohex-3-enyl methyl ketone, 1-(N-n-butylcarbamyloxymethyl)-cyclohex-3-enyl methyl ketone, 1-(N-isopropylcarbamyloxymethyl)-cyclohex-3-enyl methyl ketone, 1-(N-n-butylcarbamyloxymethyl)-cyclohexyl methyl ketone, 1-(N-isopropylcarbamyloxymethyl)-cyclohexyl methyl ketone, exo-2-(N-n-pentylcarbamyloxymethyl)-norborn-5-en-2-yl methyl ketone, exo-2-[N-(3-methylbut-2-yl)-carbamyloxymethyl]-norborn-5-en-2-yl methyl ketone, exo-2-(N-allylcarbamyloxymethyl)-norborn-5-en-2-yl methyl ketone, exo-2-(N-propargylcarbamyloxymethyl)-norborn-5-en-2-yl methyl ketone, exo-2-[N-(cyclopropylmethyl)-carbamyloxymethyl]-norborn-5-en-2-yl methyl ketone, exo-2-(N-cyclobutylcarbamyloxymethyl) -norborn-5-en-2-yl methyl ketone, exo-2-[N-(2-chloroethyl)-carbamyloxymethyl]-norborn-5-en-2-yl methyl ketone, 1-(N-cyclopropylcarbamyloxymethyl)-cyclohex-3-en-1-yl methyl ketone, 1-(N-but-2-yl-carbamyloxymethyl)-cyclohex-3-en-1-yl methyl ketone and 2-[N-(cyclobutylmethyl)-carbamyloxymethyl]-norborn-5-en-2-yl methyl ketone.

Accordingly, the present invention also relates to therapeutic agents or pharmaceutical formulations which in addition to the conventional carriers or diluents contain a compound of the formula I as the active compound, and to the use of the novel compounds as hypnotics in the treatment of sleep disturbance, and as sedatives.

The therapeutic agents or formulations are prepared in a conventional manner, by compounding an appropriate dose with the conventional carriers or diluents and the conventional pharmaceutical auxiliaries, in accordance with the desired route of administration.

The dosage depends on the age, condition and weight of the patient and on the route of administration. As a rule, the dose is from 20 to 500 mg, those in the lower range being more appropriate for sedation and those in the higher range more appropriate for a hypnotic effect.

The preferred formulations are those suitable for oral administration. Examples of these are tablets, film tablets, dragees, capsules, pills, powders, granules, solutions, suspensions and forms which exert a depot effect.

Of course, formulations for parenteral administration, eg. injection solutions, are also suitable. Suppositories are a further example of suitable formulations.

Appropriate tablets can be obtained, for example, by mixing the active compound with conventional auxiliaries, for example inert diluents, eg. dextrose, sugar, lactose, sorbitol, mannitol or polyvinylpyrrolidone, disintegrating agents, eg. corn starch or alginic acid, binders, eg. starch or gelatin, lubricants, eg. magnesium stearate or talc, and/or agents added in order to achieve a depot effect, eg. carboxypolymethylene, carboxymethylcellulose, cellulose acetate phthalate or polyvinyl acetate.

Examples of further conventional additives are preservatives, antioxidants, flavor-improving additives, stabilizers, emulsifiers, wetting agents and the like. Of course all materials used in the preparation of pharmaceutical formulations must be non-toxic and compatible with the active compounds used (cf. L. G. Goodman, A. Gilman, The Pharmacological Basis of Therapeutics).

Accordingly, dragees may be prepared by coating cores, prepared in a similar manner to the tablets, with agents conventionally used in dragee coatings, eg. polyvinylpyrrolidone, shellac, gum arabic, talc, titanium dioxide or sugar. The dragee shell can also consist of several layers, in which the auxiliaries, mentioned above in connection with tablets, may be used.

Solutions or suspensions of the novel active compounds may additionally contain flavor improvers, such as saccharin, cyclamates or sugars, and, for example, aromatics, such as vanillin or orange extract. They may also contain suspending assistants, such as sodium carboxymethylcellulose, or preservatives, such as p-hydroxybenzoates. Capsules containing an active compound may be prepared, for example, by mixing the active compound with an inert carrier, such as lactose or sorbitol, and filling gelatin capsules with the mixture.

Suitable suppositories may be prepared, for example, by mixing the active compound with a suitable carrier, such as a neutral fat or polyethylene glycol or derivative thereof.

The Examples which follow illustrate the preparation of the novel compounds without however restricting the scope of the invention to the individual Examples given. The structure of the compounds is confirmed by analyses and by spectroscopic methods (infrared and nuclear magnetic resonance).

Experimental section

A. Preparation of starting compounds

EXAMPLES I to XII glacial acetic acid, the solvent is then distilled off under reduced pressure and the residue is distilled, again under reduced pressure. If substantial formation of by-products is observed, the reaction may be stopped at a lower conversion. (During distillation, expulsion of formaldehyde gas is sometimes observed, especially if a substantial excess of formaldehyde has been employed). The yield of keto-alcohol of the formula II is 50–90%.

Keto-alcohols in which the two radicals A form a bridge over the six-membered ring are in general obtained as a mixture of the exo- and endo-isomers. According to NMR spectroscopy and exo/endo ratio is from 9:1 to 1:2. The nomenclature exo and endo refers to the position of the $CH_2OH$ group on the bridged six-membered ring. The mixtures can be separated by recrystallization or column chromatography (cf. Examples XIII to XV).

Examples I to XII (formula II) were obtained by the above method.

| Example No. | A,A | Ring double bond or hydrogenated double bond | $R^2$ | $R^3$ | $R^4$ | b.p. [°C./mm Hg][a] or m.p. [°C.][c] | Analysis | C | H | O |
|---|---|---|---|---|---|---|---|---|---|---|
| I | $-CH_2-$ | $CH=CH$ | $CH_3$ | H | H | 105–107/0.1 | calc. | 72.25 | 8.49 | 19.25 |
| | | | | | | | found. | 72.6 | 8.7 | 18.7 |
| | | | | | | | $C_{10}H_{14}O_2$ | M. Wt. = 166 | | |
| II | $-CH_2-$ | $CH=CH$ | $C_2H_5$ | H | H | 110–115/0.1 | calc. | 73.30 | 8.95 | 17.75 |
| | | | | | | | found. | 73.1 | 8.8 | 17.7 |
| | | | | | | | $C_{11}H_{16}O_2$ | M. Wt. = 180 | | |
| III | $-CH_2-$ | $CH=CH$ | $iC_3H_7$ | H | H | 96–97/0.1 | calc. | 74.19 | 9.34 | 16.47 |
| | | | | | | | found. | 73.7 | 9.1 | 16.8 |
| | | | | | | | $C_{12}H_{18}O_2$ | M. Wt. = 194 | | |
| IV | $-CH_2-$ | $CH=CH$ | $CH_2CH(CH_3)_2$ | H | H | 120–121/0.1 | calc. | 75.0 | 9.6 | 15.3 |
| | | | | | | | found. | 74.8 | 9.6 | 15.0 |
| | | | | | | | $C_{13}H_{20}O_2$ | M. Wt. = 208 | | |
| V | $-CH_2-$ | $CH_2-CH_2$ | $CH_3$ | H | H | 104–108/2 | calc. | 71.39 | 9.59 | 19.02 |
| | | | | | | | found. | 71.1 | 9.8 | 19.4 |
| | | | | | | | $C_{10}H_{16}O_2$ | M. Wt. = 168 | | |
| VI | 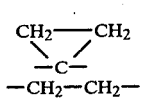 | $CH=CH$ | $CH_3$ | H | H | 115–120/0.2 | | | | |
| VII | $-CH_2-CH_2-$ | $CH=CH$ | $CH_3$ | H | H | 125–129/0.3 | calc. | 73.30 | 8.95 | 17.75 |
| | | | | | | | found. | 73.6 | 8.6 | 17.7 |
| | | | | | | | $C_{11}H_{16}O_2$ | M. Wt. = 180 | | |
| VIII | $CH_2-CH_2$ | $CH_2-CH_2$ | $CH_3$ | H | H | 43–44 | calc. | 72.49 | 9.95 | 17.56 |
| | | | | | | | found. | 72.4 | 9.7 | 17.7 |
| | | | | | | | $C_{11}H_{18}O_2$ | M. Wt. = 182 | | |
| IX | H,H | $CH=CH$ | $CH_3$ | H | H | 127–131/0.2 | calc. | 70.10 | 9.15 | 20.75 |
| | | | | | | | found. | 70.8 | 9.1 | 20.0 |
| | | | | | | | $C_9H_{14}O_2$ | M. Wt. = 154 | | |
| X | H,H | $CH=CH$ | $C_2H_5$ | H | H | 90–100/0.1[b] | | | | |
| XI | H,H | $C=C$ | $CH_3$ | 3-$CH_3$ | 4-$CH_3$ | 124–126/0.5 | calc. | 72.49 | 9.95 | 17.56 |
| | | | | | | | found. | 71.8 | 9.6 | 18.3 |
| | | | | | | | $C_{11}H_{18}O_2$ | M. Wt. = 182 | | |
| XII | H,H | $CH_2-CH_2$ | $CH_3$ | H | H | 110–113/0.1 | calc. | 69.2 | 10.2 | 20.5 |
| | | | | | | | found. | 68.8 | 10.0 | 20.7 |
| | | | | | | | $C_9H_{16}O_2$ | M. Wt. = 156 | | |

[a] It is to be noted that the actual pressure in the distillation apparatus is somewhat higher than the pressure measured at the pump, due to the elimination of formaldehyde.
[b] In the preparation of this keto-alcohol, the formation of the desired compound was accompanied by that of the keto-alcohol positional isomer, ie. cyclohex-3'-en-1'-yl 1-hydroxy-prop-2-yl ketone. The isomers were separated by column chromatography on silica gel, with a 1:3 ethyl acetate/cyclohexane mixture as the eluant.
[c] exo-endo ratio (according to NMR): Example I ~ 5:1; Examples II–IV, and VI ~ 1:1; Example V and VII ~ 3:1–4:1.

General method of preparation of a keto-alcohol of the general formula II.

A mixture of 1.0 mole of a ketone of the general formula VI and 0.5–4 moles of formaldehyde, in the form of an aqueous 35–40% strength solution, is rendered homogeneous by means of 20–100 ml of ethanol, and the pH is brought to 10–12 with a solution of potassium hydroxide in methanol. The mixture is kept for several days at room temperature, the pH being checked. When, after from about 2 to 10 days, the ketone has, according to thin layer chromatography, been substantially converted, the mixture is neutralized with EXAMPLES XIII to XVII Keto-alcohols of the formula II

EXAMPLE XIII

Exo-2-hydroxymethylnorborn-5-en-2-yl methyl ketone

A small amount of an n-hexane/ethyl acetate mixture is added, at room temperature, to 250 g of 2-hydroxymethylnorborn-5-en-2-yl methyl ketone from Example I. On storing the solution in a refrigerator, a crystalline substance slowly precipitates; it is filtered off (giving 160 g of material of melting point 34°–37° C.) and is recrystallized from n-hexane/ethyl acetate. The recrystallized material, which according to thin layer chromatography (eluant: a 1:1 ethyl acetate/cyclohexane mixture; silica gel plates) and NMR spectroscopy is the pure exo-isomer, has a melting point of 44°–45° C. On concentrating the mother liquor, additional crystalline material is obtained. NMR (CDCl$_3$, 60 MHz): δ=1.2–1.9 ppm (m, 4H); 2.0 (s, 3H, CH$_3$CO), 2.5–3.0 (m, 2H+OH); 3.75 (m, 2H, CH$_2$-O); 5.75–6.2 (m, 2H, —CH═CH—).

Analysis: calc. 72.25% C, 8.49% H, 19.25% 0: found. 72.1% C, 8.4% H, 19.6% O, C$_{10}$H$_{14}$O$_2$ M.Wt.=166.

EXAMPLE XIV

Endo-2-hydroxymethyl-norborn-5-en-2-yl methyl ketone

The combined mother liquors from the isolation of the exo-2-hydroxymethyl-norborn-5-en-2-yl methyl ketone (Example XIII) are chromatographed on silica gel, using a 1:3 ethyl acetate/cyclohexane mixture. The oil obtained is pure endo-2-hydroxymethyl-norborn-5-en-2-yl methyl ketone, according to NMR spectra and thin layer chromatography.

NMR (CDCl$_3$, 60 MHz): 0.65–1.55 (m, 3H); 1.88–2.2 (dd, 1H); 2.18 (s, 3H, CH$_3$CO); 2.6–3.2 (m, 2H+OH); 3.45 (s, 2H, CH$_2$O); 5.85–6.25 (m, 2H, CH═CH).

EXAMPLE XV

Exo-2-hydroxymethylnorborn-2-yl methyl ketone

Using a similar method to Example XIII, pure exo-2-hydroxy-methyl-norborn-2-yl methyl ketone, of melting point 48°–50° C., was obtained by recrystallization from the exo/endo mixture from Example V.

Analysis : calc. 71.39;1 % C, 9.59% H, 19.02% O: found. 71.7% C, 9.6% H, 19.2% O: C$_{10}$H$_{16}$O$_2$ M.Wt.=168

EXAMPLE XVI 3,4-Dimethyl-1-hydroxymethyl-cyclohex-3-enyl isobutyl ketone

A mixture of 65.6 g (0.338 mole) of 3,4-dimethylcyclohex-3-enyl isobutyl ketone (Example XXII), 120 ml of ethanol and 109.6 g of 37% strength formaldehyde solution (=1.35 moles) is brought to a pH of 11-12 with a 15% strength solution of potassium hydroxide in methanol, and is then refluxed for 44 hours, the pH being checked. Thereafter the solution is brought to pH 5 with glacial acetic acid and the solvent is distilled off under reduced pressure. Water is added to the residue and after saturation with sodium chloride the mixture is extracted five times with toluene. The organic phases are dried over anhydrous sodium sulfate, the solvent is distilled off on a rotary evaporator and the residue is distilled under reduced pressure. 37.7 g of 3,4-dimethyl-1-hydroxy-methyl-cyclohex-3-enyl isobutyl ketone pass over at 112°–116° C./0.1 mm Hg.

EXAMPLE XVII

2-Hydroxymethyl-bicyclo-[2.2.2]-oct-2-yl methyl ketone

A solution of 10 g of 2-hydroxymethyl-bicyclo-[2.2.2]-oct-5-en-2-yl methyl ketone (Example VII) in 50 ml of methanol is hydrogenated at room temperature, by means of hydrogen in the presence of 1 g of a 1% strength palladium/charcoal catalyst, until the absorption of hydrogen has ceased. The catalyst is filtered off, the solvent is then distilled off, and the residue (9.1 g=90%) is purified by column chromatography on silica gel (eluant: a 1:1 ethyl acetate/cyclohexane mixture). Pure 2-hydroxy-methyl-bicyclo-[2.2.2]-octyl methyl ketone of melting point 43°–44° C. is obtained; the product is identical with the substance from Example VIII.

EXAMPLES XVIII TO XXI

Phenyl carbonates of the general formula IV
(R$^5$=OC$_6$H$_5$).

EXAMPLE XVIII (2-Acetylnorborn-5-en-2-yl)-methyl phenyl carbonate (exoisomer)

A mixture of 265.6 g (1.6 moles) of exo-2-hydroxymethyl-norborn-5-en-2-yl methyl ketone (Example XIII), 400 ml of absolute tetrahydrofuran, 342 g (1.6 moles) of diphenyl carbonate and 242 g (2.4 moles) of triethylamine is stirred for 8 hours, under gentle reflux. After distilling off the solvent under reduced pressure, the residue is taken up in ether and the solution is extracted five times with 5% strength sodium hydroxide solution. The organic phase is then washed neutral with water and is dried over sodium sulfate.

After distilling off the solvent, 418 g (=91.2%) of a crystalline residue are obtained; this material is recrystallized from 1,500 ml of ether. 150 g (=33%) of (2-acetyl-norborn-5-en-2-yl)-methyl phenyl carbonate of melting point 76°–77° C. are obtained. Additional material is obtained from the mother liquors.

Analysis calc. 71.3% C, 6.3% H, 22.4% O: found. 72.0% C, 6.3% H, 22.4% O: C$_{17}$H$_{18}$O$_4$ M.Wt.=286.

EXAMPLE XIX (2-Acetyl-bicyclo-[2.2.2]-oct-5-en-2-yl)-methyl phenyl carbonate Using a method similar to Example XVIII, 2-hydroxymethyl-bicyclo-[2.2.2]-oct-5-en-2-yl methyl ketone (Example VII) gives (2-acetyl-bicyclo-[2.2.2]-oct-5-en-2-yl)-methyl phenyl carbonate, of melting point 58°–60° C.

Analysis calc. 71.98% C, 6.71% H, 21.31% O: found. 72.8% C, 6.8% H, 20.3% O: C$_{18}$H$_{20}$O$_4$ M.Wt.=300.

EXAMPLE XX (1-Acetylcyclohex-3-en-yl)-methyl phenyl carbonate

Using a method similar to Example XVIII, (1-acetyl-cyclohex-3-enyl)-methyl phenyl carbonate is obtained from 1-hydroxymethylcyclohex-3-enyl methyl ketone (Example IX). The crude product is purified by column chromatography (using a 1:5 ethyl acetate/cyclohexane mixture as the eluant; silica gel).

Analysis calc. 70.05% C, 6.61% H, 23.33% O: found. 69.9% C, 6.8% H, 23.2% O: C$_{16}$H$_{18}$O$_4$ M.Wt.=274.3.

EXAMPLE XXI (2-Acetylbicyclo-[2.2.2]-octyl)-methyl phenyl carbonate

A mixture of 11 g of the compound from Example XIX, 50 ml of methanol and 1 g of a palladium/charcoal catalyst (containing 10% of palladium) is hydrogenated at 20°–30° C. until the absorption of hydrogen has ceased; this requires about 2.5 hours. After filtering off the catalyst, the solvent is distilled off under reduced pressure and the residue (9.3 g =84%) is recrystallized from petroleum ether. 5.2 g of (2-acetylbicyclo-[2.2.2]-octyl)-methyl phenyl carbonate of melting point 74°–75° C. are obtained.

Analysis calc. 71.49% C, 7.33% H, 21.16% O: found. 71.7% C, 7.5% H, 20.8% O: $C_{18}H_{22}O_4$ M.WT.=302.4.

EXAMPLE XXII to XXIV

Ketones of the general formula VI

The ketones of the general formula VI, of which a high proportion are known from the literature, can be prepared by methods also known from the literature, for example by a Diels-Alder reaction.

EXAMPLE XXII 3,4-Dimethylcyclohex-3-en-1-yl isobutyl ketone 45.3 g of 2,3-dimethylbutadiene are added to 47.5 g of 5-methyl-hex-1-en-3-one at initially 100° C., at a rate such that the temperature does not drop below 90° C. The mixture is then kept for 1 hour at 100° C. and 30 minutes at 115° C., the excess dimethylbutadiene is distilled off, and the residue is distilled under reduced pressure. 64 g of 3,4-dimethylcyclohex-3-en-1-yl isobutyl ketone, of boiling point 99°–101° C./3 mm Hg, are obtained.

EXAMPLE XXIII 7,7-(1,2-Ethylidene)-norborn-5-en-2-yl methyl ketone 20.5 g of spiro-[2,4]-hepta-3,5-diene are heated to 60° C. and 16.45 g of methyl vinyl ketone are added. The mixture is then stirred for 4 hours at 60° C., after which it is distilled under reduced pressure. 26.6 g (=76.4%) of 7,7-(1,2-ethylidene)-norborn-5-en-2-yl methyl ketone, of boiling point 90°–92° C./6 mm Hg, are obtained.

EXAMPLE XXIV

Cyclohex-3-enyl ethyl ketone 50 g of pent-1-en-3-one and 50 g of butadiene are reacted, in the presence of 1 g of hydroquinone, in a 250 ml shaken bomb, at 100° C. After 5 hours, the bomb is cooled and the product is distilled. 55 g=76% of cyclohex-3-enyl ethyl ketone, of boiling point 78°–81° C./10 mm Hg, are obtained.

B. Compounds according to the invention

EXAMPLES 1 to 77

Preparation by reaction of a keto-alcohol II with an isocyanate III

EXAMPLE 1

2-Exo-(N-methylcarbamyloxymethyl)-norborn-5-en-2-yl methyl ketone 6.3 g of methyl isocyanate and 0.08 g of tin-(II) octanoate are added to a solution of 16.6 g of 2-exohydroxymethylnorborn-5-en-2-yl methyl ketone (Example XIII) in 25 ml of absolute tetrahydrofuran, at room temperature. After 20 hours, the solvent is distilled off and the residue (23 g=100%) is distilled at 170° C./0.01 mm Hg. 13.8 g of a crystalline substance of melting point 51.5°–52.5° C. are obtained.

Analysis calc. 64.57% C, 7.62% H, 6.28% N, 21.52% 0: found. 64.4% C, 7.6% H, 6.4% N, 21.2% O: $C_{12}H_{17}NO_3$ M.Wt.=223.

EXAMPLES 2 to 72

General method for the reaction of a keto-alcohol of the formula II with an isocyanate of the formula III.

1% by weight, based on keto-alcohol employed, of dibutyl-tin diacetate, followed by 0.045–0.055 mole of an isocyanate of the formula III ($R^1$=H), which may or may not be diluted with a small amount of THF or ether, are added dropwise to a solution of 0.05 mole of a ketoalcohol II in 10–30 ml of absolute tetrahydrofuran or ether, at room temperature. In many cases, the temperature of the reaction mixture rises by 10°–20° C. After completion of the reaction (which requires from 10 minutes to a few hours, at from +20° to +40° C.), completion being established by thin layer chromatography, the solvent is stripped off under reduced pressure and a small amount of ether or ethyl acetate/cyclohexane is added to the residue. Crystalline products are purified by recrystallization (see the Table which follows, 3rd column, R (=recrystallization): solvent), and oily products by column chromatography over silica gel (see the Table which follows, 3rd column, CC (=column chromatography): eluant). In some cases, the products crystallize after column chromatography. The yields of pure product are in the range of from 50 to 95%.

The compounds of Examples 2 to 72, given below, were prepared by this method.

Examples 2 to 21: Reaction of exo-2-hydroxymethylnorborn-2-en-5-yl methyl ketone (Example XIII) with an isocyanate $R^1$NCO

| Example No. | $R^1$ | Purification of the crude product | m.p. [°C.] | Analysis | | | |
|---|---|---|---|---|---|---|---|
| | | | | C | H | N | O |
| 2 | CH$_3$ | R: cyclohexane/ether | 52–52.5 | identical with the substance from Example 1 | | | |
| 3 | C$_2$H$_5$ | R: ether | 41–42 | calc. 65.8 | 8.1 | 5.9 | 20.1 |
| | | | | found. 65.6 | 8.0 | 5.8 | 20.2 |
| | | | | $C_{13}H_{19}NO_3$ | | M. Wt. = 237 | |
| 4 | n-C$_3$H$_7$ | R: ether + a small amount of cyclohexane | 57–59 | calc. 66.9 | 8.4 | 5.6 | 19.1 |
| | | | | found. 67.1 | 8.4 | 5.4 | 19.0 |
| | | | | $C_{14}H_{21}NO_3$ | | M. Wt. = 251 | |
| 5 | n-C$_4$H$_9$ | R: ethyl acetate/hexane | 46–47 | calc. 67.92 | 8.68 | 5.28 | 18.11 |
| | | | | found. 67.8 | 8.5 | 5.8 | 18.2 |
| | | | | $C_{15}H_{23}NO_3$ | | M. Wt. = 265.3 | |
| 6 | n-C$_6$H$_{13}$ | R: n-hexane | 35–36 | calc. 69.6 | 9.2 | 4.8 | 16.4 |
| | | | | found. 70.0 | 9.1 | 4.8 | |
| | | | | $C_{17}H_{27}NO_3$ | | M. Wt. = 293 | |
| 7 | i-C$_3$H$_7$ | R: ethyl acetate/n-hexane | 84–85 | calc. 66.93 | 8.37 | 5.58 | 19.12 |
| | | | | found. 66.8 | 8.3 | 6.1 | 19.1 |
| | | | | $C_{14}H_{21}NO_3$ | | M. Wt. = 251.3 | |
| 8 | t-C$_4$H$_9$ | R: petroleum ether | 67–69 | calc. 67.9 | 8.7 | 5.3 | 18.1 |

-continued

Examples 2 to 21: Reaction of exo-2-hydroxymethylnorborn-2-en-5-yl methyl ketone (Example XIII) with an isocyanate R¹NCO

| Example No. | R¹ | Purification of the crude product | m.p. [°C.] | Analysis | | | | |
|---|---|---|---|---|---|---|---|---|
| | | | | | C | H | N | O |
| 9 | $CH_2=CH-$ | R: ethyl acetate | 65–66 | found. | 67.8 | 8.8 | 5.4 | 18.1 |
| | | | | | $C_{15}H_{23}NO_3$ | | M. Wt. = 265 | |
| | | | | calc. | 66.4 | 7.3 | 6.0 | 20.4 |
| | | | | found. | 66.3 | 7.1 | 6.0 | 20.5 |
| 10 | $CH_3-CH=CH-$ | R: 1:1 ethyl acetate/cyclohexane | 64–65 | | $C_{13}H_{17}NO_3$ | | M. Wt. = 235 | |
| 11 | $(CH_3)_2C=CH-$ | R: ethyl acetate/n-hexane | 76–78 | calc. | 68.42 | 8.04 | 5.32 | 18.23 |
| | | | | found. | 68.2 | 8.1 | 5.3 | 18.7 |
| | | | | | $C_{15}H_{21}NO_3$ | | M. Wt. = 263 | |
| 12 | $CH_3OCH_2-$ | R: cyclohexane + a small amount of ethyl acetate | 51–52 | calc. | 61.6 | 7.6 | 5.5 | 25.3 |
| | | | | found. | 61.5 | 7.5 | 5.6 | 25.3 |
| | | | | | $C_{13}H_{19}NO_4$ | | M. Wt. = 253 | |
| 13 | $CH_3SCH_2CH_2-$ | CC: 3:7 ethyl acetate/cyclohexane | oil | calc. | 59.34 | 7.47 | 4.94 | 16.4 |
| | | | | found. | 58.7 | 7.3 | 4.9 | 17.5 |
| | | | | | $C_{14}H_{21}NO_3S$ | | M. Wt. = 283 | |
| 14 | (methyl-cyclohexyl-CH₂–) | CC: 3:7 ethyl acetate/cyclohexane | oil | calc. | 73.5 | 9.3 | 3.9 | 13.4 |
| | | | | found. | 73.0 | 9.2 | 3.6 | 14.2 |
| | | | | | $C_{22}H_{33}NO_3$ | | M. Wt. = 360 | |
| 15 | (cyclopentyl) | R: ethyl acetate | 98–99 | calc. | 69.3 | 8.4 | 5.0 | 17.3 |
| | | | | found. | 69.0 | 8.4 | 5.3 | 16.9 |
| | | | | | $C_{16}H_{23}NO_3$ | | M. Wt. = 277 | |
| 16 | (dimethyl-cyclohexyl) | CC: 1:1 ethyl acetate/cyclohexane | oil | calc. | 72.5 | 8.8 | 4.2 | 14.5 |
| | | | | found. | 72.1 | 8.5 | 4.0 | 15.2 |
| | | | | | $C_{20}H_{29}NO_3$ | | M. Wt. = 331 | |
| 17 | $C_6H_5-$ | R: ethyl acetate/hexane | 92–92.5 | calc. | 71.58 | 6.67 | 4.91 | 16.84 |
| | | | | found. | 71.5 | 6.3 | 5.4 | 16.9 |
| | | | | | $C_{17}H_{19}NO_3$ | | M. Wt. = 285 | |
| 18 | $p-Cl-C_6H_4$ | R: ethyl acetate | 149–151 | calc. | 63.8 | 5.6 | 4.4 | 15.0 Cl 11.1 |
| | | | | found. | 63.7 | 5.7 | 4.7 | 14.7   11.3 |
| | | | | | $C_{17}H_{18}ClNO_3$ | | M. Wt. = 319.5 | |
| 19 | $Cl_2C=CH-$ | R: ether/n-hexane | 80–81 | calc. | 51.33 | 4.97 | 4.60 | 15.78 Cl 23.31 |
| | | | | found. | 51.5 | 5.1 | 4.8 | 15.8    23.2 |
| | | | | | $C_{13}H_{15}ClNO_3$ | | M. Wt. = 304 | |
| 20 | (tetrahydropyranyl) | R: ethyl acetate/n-hexane | 115–116 | calc. | 65.51 | 7.90 | 4.77 | 21.81 |
| | | | | found. | 65.1 | 7.8 | 5.1 | 21.8 |
| | | | | | $C_{16}H_{23}NO_4$ | | M. Wt. = 293 | |
| 21 | (cyclopropyl-CH(C₆H₅)–) | CC: 3:7 ethyl acetate/cyclohexane | oil | calc. | 73.82 | 7.12 | 4.30 | 14.75 |
| | | | | found. | 74.0 | 7.2 | 4.2 | 14.3 |
| | | | | | $C_{20}H_{23}NO_3$ | | M. Wt. = 325 | |

EXAMPLE 22

2-Endo-(N-isopropylcarbamyloxymethyl)-norborn-5-en-2-yl methyl ketone.

Following the general method, endo-2-hydroxymethyl-norborn-5-en-2-yl methyl ketone (Example XIV) and isopropyl isocyanate give 2-endo-(N-isopropylcarbamyloxy-2-methyl)-norborn-5-en-2-yl methyl ketone as an oil. This is purified by column chromatography over silica gel, with a 3:7 ethyl acetate/cyclohexane mixture as the eluant.

Analysis calc. 66.93% C, 8.37% H, 5.58% N, 19.12% O: found. 66.8% C, 8.4% H, 5.9% N, 19.3% O: $C_{14}H_{21}NO_3$ M.Wt.=251.

| Example No. | R¹ | Purification of the crude product | m.p. [°C.] | Analysis | | | | |
|---|---|---|---|---|---|---|---|---|
| | | | | | C | H | N | O |
| Examples 23 to 25: | | reaction of 2-hydroxymethyl-norborn-5-en-2-yl ethyl ketone (Example II) with an isocyanate R¹NCO | | | | | | |
| 23 | $CH_3$ | CC: 1:3 ethyl acetate/cyclohexane | oil | calc. | 65.80 | 8.07 | 5.90 | 20.23 |
| | | | | found. | 65.6 | 7.9 | 6.0 | 20.3 |
| | | | | | $C_{13}H_{19}NO_3$ | | M. Wt. = 237 | |
| 24 | $C_2H_5$ | CC: 1:5 ethyl acetate/cyclohexane | oil | calc. | 66.91 | 8.42 | 5.57 | 19.10 |
| | | | | found. | 66.4 | 8.2 | 5.5 | |
| | | | | | $C_{14}H_{21}NO_3$ | | M. Wt. = 251 | |

-continued

| Example No. | R¹ | Purification of the crude product | m.p. [°C.] | Analysis | | | |
|---|---|---|---|---|---|---|---|
| | | | | | C | H | N | O |
| 25 | i-C₃H₇ | CC: 1:5 ethyl acetate/cyclohexane | oil | calc. found. | 67.90 67.5 $C_{15}H_{23}NO_3$ | 8.74 8.6 M. Wt. | 5.28 5.3 = 265 | 18.09 18.8 |
| Examples 26 to 28: | | reaction of 2-hydroxymethyl-norborn-5-en-2-yl isopropyl ketone (Example III) with an isocyanate R¹NCO | | | | | | |
| 26 | CH₃ | R: n-hexane/cyclohexane | 78–79 | calc. found. | 66.91 66.8 $C_{14}H_{21}NO_3$ | 8.42 8.4 M. Wt. | 5.57 5.5 = 251 | 19.10 19.4 |
| 27 | C₂H₅ | R: n-hexane/cyclohexane | 77–78 | calc. found. | 67.90 67.7 $C_{15}H_{23}NO_3$ | 8.75 8.7 M. Wt. | 5.28 5.2 = 265 | 18.09 18.4 |
| 28 | i-C₃H₇ | R: n-hexane | 80–81 | calc. found. | 68.79 68.6 $C_{16}H_{25}NO_3$ | 9.02 9.0 M. Wt. | 5.01 5.2 = 279 | 17.18 17.3 |
| Examples 29 to 31: | | reaction of 2-hydroxymethyl-norborn-5-en-2-yl isobutyl ketone (Example IV) with an isocyanate R¹NCO | | | | | | |
| 29 | CH₃ | R: 1:1 n-hexane/cyclohexane | 78–79 | calc. found. | 67.90 67.9 $C_{15}H_{23}NO_3$ | 8.74 8.7 M. Wt. | 5.28 5.5 = 265 | 18.09 17.8 |
| 30 | C₂H₅ | R: 1:1 n-hexane/cyclohexane | 59–60 | calc. found. | 68.79 68.9 $C_{16}H_{25}NO_3$ | 9.02 8.9 M. Wt. | 5.01 5.3 = 279 | 17.18 17.3 |
| 31 | i-C₃H₇ | R: 1:1 n-hexane/cyclohexane | 70–71 | calc. found. | 69.59 69.3 $C_{17}H_{27}NO_3$ | 9.28 9.3 M. Wt. | 4.77 5.3 = 293 | 16.36 16.2 |
| Examples 32 to 38: | | reaction of exo-2-hydroxymethylnorborn-2-yl methyl ketone (Example XV) with an isocyanate R¹NCO | | | | | | |
| 32 | CH₃ | R: ethyl acetate | 53–54 | calc. found. | 63.98 63.5 $C_{12}H_{19}NO_3$ | 8.49 8.5 M. Wt. | 6.22 6.4 = 225 | 21.31 22.0 |
| 33 | C₂H₅ | CC: 1:9 ethyl acetate/cyclohexane | 40–41 | calc. found. | 65.25 65.1 $C_{13}H_{21}NO_3$ | 8.84 8.7 M. Wt. | 5.85 5.8 = 239 | 20.06 |
| 34 | n-C₃H₇ | R: petroleum ether | 49–50 | calc. found. | 66.4 66.5 $C_{14}H_{23}NO_3$ | 9.2 9.0 M. Wt. | 5.5 5.5 = 253 | 18.9 19.1 |
| 35 | n-C₄H₉ | CC: 2:3 ethyl acetate/cyclohexane | oil | calc. found. | 67.4 67.0 $C_{15}H_{25}NO_3$ | 9.4 9.4 M. Wt. | 5.2 5.3 = 267 | 18.0 |
| 36 | i-C₃H₇ | R: ethyl acetate | 79–80 | calc. found. | 66.4 66.1 $C_{14}H_{23}NO_3$ | 9.2 9.1 M. Wt. | 5.5 5.9 = 253 | 18.9 |
| 37 | CH₃OCH₂— | (1) R: hexane/toluene (2) CC: 3:7 ethyl acetate/cyclohexane | 51–52 | calc. found. | 61.3 59.7 $C_{13}H_{21}NO_4$ | 7.9 7.9 M. Wt. | 5.3 5.7 = 255 | 25.4 |
| 38 | (cyclopentyl) | R: ethyl acetate | 92–93 | calc. found. | 68.8 68.8 $C_{16}H_{25}NO_3$ | 9.0 8.9 M. Wt. | 5.0 5.1 = 279 | 17.2 |
| Examples 39 to 40: | | reaction of 7,7-(1,2-ethylidene)-2-hydroxymethylnorborn-5-en-2-yl methyl ketone (Example VI) with an isocyanate R¹NCO | | | | | | |
| 39 | C₂H₅ | CC: 3:7 ethyl acetate/cyclohexane | oil | calc. found. | 68.42 69.3 $C_{15}H_{21}NO_3$ | 8.04 8.1 M. Wt. | 5.32 5.1 = 263 | 18.23 18.4 |
| 40 | i-C₃H₇ | CC: 3:7 ethyl acetate/cyclohexane | oil | calc. found. | 69.29 69.3 $C_{16}H_{23}NO_3$ | 8.36 8.0 M. Wt. | 5.05 5.0 = 277 | 17.30 18.0 |
| Examples 41 to 45: | | reaction of 2-hydroxymethylbicyclo-[2.2.2]-oct-5-en-2-yl methyl ketone (Example VII) with an isocyanate R¹NCO | | | | | | |
| 41 | C₂H₅ | CC: 1:7 ethyl acetate/cyclohexane | oil | calc. found. | 66.91 66.7 $C_{14}H_{21}NO_3$ | 8.42 8.5 M. Wt. | 5.57 5.6 = 251 | 19.10 19.2 |
| 42 | n-C₃H₇ | CC: 1:5 ethyl acetate/cyclohexane | oil | calc. found. | 67.90 67.7 $C_{15}H_{23}NO_3$ | 8.74 8.8 M. Wt. | 5.28 5.7 = 265 | 18.09 18.4 |
| 43 | n-C₄H₉ | CC: 1:7 ethyl acetate/cyclohexane | oil | calc. found. | 68.79 68.5 $C_{16}H_{25}NO_3$ | 9.02 8.8 M. Wt. | 5.01 5.1 = 279 | 17.18 17.1 |
| 44 | i-C₃H₇ | R: ethyl acetate | 78–80 | calc. found. | 67.90 67.5 $C_{15}H_{23}NO_3$ | 8.74 9.2 M. Wt. | 5.28 5.6 = 265 | 18.09 17.9 |
| 45 | CH₃OCH₂— | CC: 1:1.3 ethyl acetate/cyclohexane | 43–45 | calc. found. | 62.90 62.9 $C_{14}H_{21}NO_4$ | 7.92 8.1 M. Wt. | 5.24 5.1 = 267 | 23.94 23.9 |
| Examples 46 to 49: | | reaction of 2-hydroxymethylbicyclo-[2.2.2]-oct-2-yl methyl ketone (Example VIII) with an isocyanate R¹NCO | | | | | | |
| 46 | C₂H₅ | R: ethyl acetate/petroleum ether | 60–61 | calc. found. | 66.37 66.5 | 9.15 8.9 | 5.53 5.7 | 18.95 19.1 |

-continued

| Example No. | R¹ | Purification of the crude product | m.p. [°C] | | Analysis C | H | N | O |
|---|---|---|---|---|---|---|---|---|
| 47 | n-C$_3$H$_7$ | R: ether/n-hexane | 55–56 | calc. found. | C$_{14}$H$_{23}$NO$_3$ 67.38 67.2 | 9.42 9.4 | M. Wt. = 253 5.24 5.3 | 17.95 18.1 |
| 48 | i-C$_3$H$_7$ | R: ether | 100–102 | calc. found. | C$_{15}$H$_{25}$NO$_3$ 67.38 67.4 | 9.42 9.2 | M. Wt. = 267 5.24 5.5 | 17.95 18.1 |
| 49 | ⬠- | R: ether | 111–112 | calc. found. | C$_{15}$H$_{25}$NO$_3$ 69.59 69.6 | 9.28 8.9 | M. Wt. = 267 4.77 4.9 | 16.36 16.5 |
| Examples 50 to 58: | | reaction of 1-hydroxymethyl-cyclohex-3-en-1-yl methyl ketone (Example IX) with an isocyanate R¹NCO | | | C$_{17}$H$_{27}$NO$_3$ | | M. Wt. = 293 | |
| 50 | CH$_3$ | CC: 1:1 ethyl acetate/ cyclohexane | oil | calc. found. | 62.5 61.9 | 8.1 8.0 | 6.6 6.7 | 22.7 |
| 51 | C$_2$H$_5$ | CC: 3:7 ethyl acetate/ cyclohexane | oil | calc. found. | C$_{11}$H$_{17}$NO$_3$ 63.98 63.6 | 8.49 8.6 | M. Wt. = 211 6.22 6.3 | 21.31 22.0 |
| 52 | n-C$_3$H$_7$ | CC: 3:7 ethyl acetate/ cyclohexane | oil | calc. found. | C$_{12}$H$_{19}$NO$_3$ 65.25 65.0 | 8.84 8.5 | M. Wt. = 225 5.85 5.9 | 20.06 19.9 |
| 53 | n-C$_4$H$_9$ | CC: 2:3 ethyl acetate/ cyclohexane | oil | calc. found. | C$_{13}$H$_{21}$NO$_3$ 66.4 65.9 | 9.2 9.1 | M. Wt. = 239 5.5 5.8 | 18.9 |
| 54 | i-C$_3$H$_7$ | CC: ethyl acetate | oil | calc. found. | C$_{14}$H$_{23}$NO$_3$ 65.2 64.0 | 8.8 8.9 | M. Wt. = 253 5.9 6.4 | 20.1 |
| 55 | CH$_3$OCH$_2$ | CC: 4:7 ethyl acetate/ cyclohexane | oil | calc. found. | C$_{13}$H$_{21}$NO$_3$ 59.73 59.2 | 7.94 8.0 | M. Wt. = 239 5.80 5.8 | 26.52 |
| 56 | CH$_2$=CH— | CC: 3:7 ethyl acetate/ cyclohexane | oil | calc. found. | C$_{12}$H$_{19}$NO$_4$ 64.55 64.3 | 7.67 7.6 | M. Wt. = 241 6.27 6.3 | 21.50 |
| 57 | ⬠- | CC: 3:7 ethyl acetate/ cyclohexane | oil | calc. found. | C$_{12}$H$_{17}$NO$_3$ 67.9 67.3 | 8.7 8.9 | M. Wt. = 223 5.2 4.9 | 18.1 |
| 58 | (tetrahydropyranyl) | CC: 3:7 ethyl acetate/ cyclohexane | oil | calc. found. | C$_{15}$H$_{23}$NO$_3$ 64.04 63.4 | 8.24 8.1 | M. Wt. = 265 4.98 4.9 | 22.75 23.0 |
| | | | | | C$_{15}$H$_{23}$NO$_4$ | | M. Wt. = 281 | |

EXAMPLE 59

1-(N-Isopropylcarbamyloxymethyl)-cyclohex-3-enyl ethyl ketone

Reaction of 1-hydroxymethylcyclohex-3-enyl ethyl ketone (Example X) with isopropyl isocyanate gives 1-(N-isopropylcarbamyloxymethyl)-cyclohex-3-enyl ethyl ketone as an oil. This is purified by column chromatography over silica gel, using a 1:5 ethyl acetate/cyclohexane mixture.

Analysis calc. 66.37% C, 9.15% H, 5.53% N, 18.95% O: found. 65.9% C, 8.9% H, 5.5% N, 19.6% O: C$_{14}$H$_{23}$NO$_3$ M.Wt.=253.

| Example No. | R¹ | Purification of the crude product | m.p. [°C] | | Analysis C | H | N | O |
|---|---|---|---|---|---|---|---|---|
| Examples 60 to 65: | | reaction of 3,4-dimethyl-1-hydroxymethylcyclohex-3-enyl methyl ketone (Example XI) with an isocyanate R¹NCO | | | | | | |
| 60 | C$_2$H$_5$ | CC: 2:5 ethyl acetate/ cyclohexane | oil | calc. found. | 66.37 66.1 | 9.15 9.1 | 5.53 5.3 | 18.95 19.5 |
| 61 | n-C$_3$H$_7$ | CC: 1:3 ethyl acetate/ cyclohexane | oil | calc. found. | C$_{14}$H$_{23}$NO$_3$ 67.38 66.5 | 9.42 9.1 | M. Wt. = 253 5.24 5.3 | 17.95 18.8 |
| 62 | n-C$_4$H$_9$ | CC: 1:7 ethyl acetate/ cyclohexane | oil | calc. found. | C$_{15}$H$_{25}$NO$_3$ 68.29 67.9 | 9.67 9.4 | M. Wt. = 267 4.98 5.4 | 17.06 16.9 |
| 63 | i-C$_3$H$_7$ | CC: 1:7 ethyl acetate/ cyclohexane | oil | calc. found. | C$_{16}$H$_{27}$NO$_3$ 68.29 67.9 | 9.67 9.4 | M. Wt. = 281 4.98 5.4 | 17.06 16.9 |
| 64 | CH$_3$OCH$_2$ | CC: 1:3 ethyl acetate/ cyclohexane | oil | calc. found. | C$_{15}$H$_{25}$NO$_3$ 62.43 62.0 | 8.61 8.4 | M. Wt. = 281 5.20 5.4 | 23.76 23.8 |
| 65 | ⬡- | CC: 1:4 ethyl acetate/ cyclohexane | oil | calc. found. | C$_{14}$H$_{23}$NO$_4$ 70.32 70.3 | 9.51 9.3 | M. Wt. = 269 4.56 4.6 | 15.61 15.9 |
| | | | | | C$_{18}$H$_{29}$NO$_3$ | | M. Wt. = 307 | |
| Examples 66 to 67: | | reaction of 3,4-dimethyl-1-hydroxymethylcyclohex-3-enyl isobutyl ketone | | | | | | |

-continued

| Example No. | $R^1$ | Purification of the crude product | m.p. [°C.] | Analysis | | | |
|---|---|---|---|---|---|---|---|
| | | | | C | H | N | O |
| 66 | $C_2H_5$ | (Example XVI) with an isocyanate $R^1NCO$ CC: 1:6 ethyl acetate/ cyclohexane | oil | calc. 67.07 found. 67.1 $C_{17}H_{29}NO_3 \cdot \frac{1}{2}H_2O$ M. Wt. = 304.4 | 9.93 9.4 | 4.60 4.4 | 18.40 18.7 |
| 67 | $i-C_3H_7$ | CC: 1:6 ethyl acetate/ cyclohexane | oil | calc. 69.86 found. 69.1 $C_{18}H_{31}NO_3$ M. Wt. = 309 | 10.10 9.7 | 4.53 4.5 | 15.51 |
| Examples 68 to 72: | | reaction of 1-hydroxymethylcyclohexyl methyl ketone (Example XII) with an isocyanate $R^1NCO$ | | | | | |
| 68 | $CH_3$ | CC: 1:6 ethyl acetate/ cyclohexane | oil | calc. 61.95 found. 62.0 $C_{11}H_{19}NO_3$ M. Wt. = 213 | 8.95 9.0 | 6.57 6.9 | 22.50 22.9 |
| 69 | $C_2H_5$ | CC: 1:5 ethyl acetate/ cyclohexane | oil | calc. 63.41 found. 63.5 $C_{12}H_{21}NO_3$ M. Wt. = 227 | 9.31 9.1 | 6.16 6.0 | 21.12 21.5 |
| 70 | $n-C_4H_9$ | CC: 1:3 ethyl acetate/ cyclohexane | oil | calc. 65.85 found. 65.7 $C_{14}H_{25}NO_3$ M. Wt. = 255 | 9.87 9.5 | 5.49 5.7 | 18.80 19.3 |
| 71 | $i-C_3H_7$ | R: cyclohexane | 51–52 | calc. 64.70 found. 64.9 $C_{13}H_{23}NO_3$ M. Wt. = 241 | 9.61 9.4 | 5.80 6.2 | 19.89 19.8 |
| 72 | $t-C_4H_9$ | R: ethyl acetate/ n-hexane | 98–99 | calc. 65.85 found. 65.7 $C_{14}H_{25}NO_3$ M. Wt. = 255 | 9.87 9.4 | 5.49 5.4 | 18.80 18.8 |

EXAMPLES 73 to 77

Reaction of cyanic acid with a keto-alcohol of the general formula II

EXAMPLE 73

2-Carbamyloxymethyl-norborn-5-en-2-yl methyl ketone 52 g (0.8 mole) of sodium cyanate, followed dropwise by 95.8 g (0.84 mole) of trifluoroacetic acid, are added to a solution of 66.4 g (0.4 mole) of 2-hydroxymethyl-norborn-5-en-2-yl methyl ketone in 120 ml of methylene chloride at 20° C., with slow stirring. The mixture is then stirred for 5 hours at room temperature, after which it is diluted with water. It is then repeatedly extracted with methylene chloride and the organic phases are combined and dried over sodium sulfate. After distilling off the solvent, a crystalline residue (83.1 g=99%) is obtained, and this is recrystallized from ethyl acetate. 45.8 g of 2-carbamyloxymethylnorborn-5-en-2-yl methyl ketone, of melting point 118°–119° C., are obtained.

Analysis calc. 63.1% C, 7.2% H, 6.7% N, 22.9% O: found 63.3% C, 7.1% H, 6.8% N: $C_{11}H_{15}NO_3$ M.Wt.=209.

EXAMPLES 74 to 77

Using a method similar to Example 73, the following carbamates are prepared from the corresponding keto-alcohols of the formula II:

EXAMPLE 74

2-Carbamyloxymethylnorborn-5-en-2-yl isopropyl ketone

Melting point: 131°–133° C. (recrystallization from ethyl acetate)

Analysis calc. 65.80% C, 8.07% H, 5.90% N, 20.23% O: found 65.5% C, 7.9% H, 6.1% N, 20.1% O: $C_{13}H_{19}NO_3$ M.Wt.=237

EXAMPLE 75

2-Carbamyloxymethylnorborn-5-en-2-yl isobutyl ketone

Melting point: 81°–83° C. (recrystallization from ethyl acetate/hexane)

Analysis calc. 66.4% C, 8.9% H, 5.5% N, 19.0% O: found 66.7% C, 8.3% H, 5.7% N, 19.1% O: $C_{14}H_{23}NO_3$ M.Wt.=253.

EXAMPLE 76

1-Carbamyloxymethyl-3,4-dimethylcyclohex-3-enyl methyl ketone

Melting point: 110°–111° C. (recrystallization from petroleum ether/ethyl acetate Analysis calc. 63.98% C, 8.50% H, 6.22% N, 21.31% O: found 64.0% C, 8.2% H, 6.4% N, 21.6% O: $C_{12}H_{19}NO_3$ M.Wt.=225.

EXAMPLE 77

1-Carbamyloxymethyl-3,4-dimethylcyclohex-3-enyl isobutyl ketone

Melting point: 128°–130° C. (recrystallization from ethyl acetate/n-hexane)

Analysis calc. 67.38% C, 9.42% H, 5.24% N, 17.95% O: found 67.4% C, 9.3% H, 5.2% N, 18.14% O: $C_{15}H_{25}NO_3$ M.Wt.=267.

EXAMPLES 78 to 128

General Method for the reaction of a phenyl carbonate of the general formula IV ($R^5=OC_6H_5$) with an amine $R^1NH_2$ 0.033–0.04 mole of amine $R^1NH_2$, in the pure form, or as a solution in tetrahydrofuran or ether or, especially in the case of low-boiling amines, as an aqueous solution, is added dropwise to a solution of 0.033 mole of a phenyl carbonate of the formula IV ($R^5=OC_6H_5$) in from 5 to 30 ml of tetrahydrofuran or ether, at room temperature. After completion of the reaction, which requires from 5 minutes to 2 hours, and is ascertained by thin layer chromatography, the tetrahydrofuran is replaced by ether, where necessary, and the organic phase is extracted from two to five times with 5% strength sodium hydroxide solution and is washed once with saturated sodium chloride solution. After drying the organic phase over sodium sulfate and stripping off the solvent, the crude product obtained is in many cases crystalline (in some cases, treatment with a small amount of solvent, for example ethyl acetate/cyclohexane, is required to obtain crystalline material); this crude product is recrystallized from a suitable solvent. Oily crude products are purified by column chromatography over silica gel. The yields of pure product are from 50 to 95%.

| Example No. | $R^1$ | Purification of the crude product | m.p. [°C.] | Analysis | | | |
|---|---|---|---|---|---|---|---|
| | | | | C | H | N | O |
| Examples 78 to 118. | | Reaction of (2-acetylnorborn-5-en-2-yl)-methyl phenyl carbonate (Example XVIII) with an amine $R^1NH_2$ | | | | | |
| 78 | H | R: ethyl acetate | 118–119 | identical with substance from Example 73 | | | |
| 79 | $C_2H_5$ | R: ether | 41–42 | identical with substance from Example 3 | | | |
| 80 | n-$C_3H_7$ | R: ether/cyclohexane | 57–59 | identical with substance from Example 4 | | | |
| 81 | n-$C_4H_9$ | R: ethyl acetate/hexane | 46–47 | identical with substance from Example 5 | | | |
| 82 | n-$C_5H_{11}$ | R: n-hexane | 49–50 | calc. 68.8 | 9.0 | 5.0 | 17.2 |
| | | | | found 68.9 | 9.2 | 5.0 | |
| | | | | $C_{16}H_{25}NO_3$ | M. Wt. = 279 | | |
| 83 | n-$C_6H_{13}$ | R: n-hexane | 35–36 | identical with substance from Example 6 | | | |
| 84 | n-$C_8H_{17}$ | R: n-hexane | 49–50 | calc. 71.0 | 9.6 | 4.4 | 14.9 |
| | | | | found 71.2 | 9.5 | 4.4 | |
| | | | | $C_{19}H_{31}NO_3$ | M. Wt. = 321 | | |
| 85 | n-$C_{12}H_{25}$ | R: n-hexane | 70–71 | calc. 73.2 | 10.4 | 3.7 | 12.7 |
| | | | | found 73.4 | 10.2 | 3.7 | |
| | | | | $C_{23}H_{39}NO_3$ | M. Wt. = 377 | | |
| 86 | i-$C_3H_7$ | R: ethyl acetate/n-hexane | 84–85 | identical with substance from Example 7 | | | |
| 87 | $(CH_3)_2CH-CH_2-$ | R: cyclohexane | 55–57 | calc. 67.9 | 8.7 | 5.3 | 18.1 |
| | | | | found 68.0 | 8.7 | 5.4 | |
| | | | | $C_{15}H_{23}NO_3$ | M. Wt. = 265 | | |
| 88 | $CH_3-CH_2-CH(CH_3)-$ | R: cyclohexane | 81–82 | calc. 67.9 | 8.7 | 5.3 | 18.1 |
| | | | | found 67.8 | 8.4 | 5.1 | 18.7 |
| | | | | $C_{15}H_{23}NO_3$ | M. Wt. = 265 | | |
| 89 | $(CH_3)_2CH-CH(CH_3)-$ | CC: 1:3 ethyl acetate/cyclohexane | 80–81 | calc. 68.8 | 9.0 | 5.0 | 17.2 |
| | | | | found 69.0 | 8.8 | 5.0 | 17.1 |
| | | | | $C_{16}H_{25}NO_3$ | M. Wt. = 279 | | |
| 90 | $CH_2=CH-CH_2$ | R: cyclohexane/ethyl acetate | 51–52 | calc. 67.45 | 7.68 | 5.62 | 19.25 |
| | | | | found 67.0 | 7.2 | 5.9 | |
| | | | | $C_{14}H_{19}NO_3$ | M. Wt. = 249 | | |
| 91 | $CH_2=C(CH_3)-CH_2$ | R: hexane/ethyl acetate | 36–37 | calc. 68.4 | 8.0 | 5.3 | 18.2 |
| | | | | found 68.4 | 8.0 | 5.2 | |
| | | | | $C_{15}H_{21}NO_3$ | M. Wt. = 263 | | |
| 92 | $HC\equiv C-CH_2$ | R: cyclohexane/ethyl acetate | 48–50 | calc. 68.00 | 6.93 | 5.66 | 19.41 |
| | | | | found 68.0 | 7.0 | 5.7 | |
| | | | | $C_{14}H_{17}NO_3$ | M. Wt. = 247 | | |
| 93 | $NC-CH_2-CH_2-$ | CC: 1:3 ethyl acetate/cyclohexane | oil | calc. 64.11 | 6.92 | 10.68 | 18.30 |
| | | | | found 63.9 | 6.9 | 10.8 | 18.7 |
| | | | | $C_{14}H_{18}N_2O_3$ | M. Wt. = 262 | | |
| 94 | $CH_3OCH_2CH(CH_3)-$ | CC: 1:3 ethyl acetate/cyclohexane | oil | calc. 64.04 | 8.24 | 4.98 | 22.74 |
| | | | | found 64.2 | 8.1 | 4.9 | 23.2 |
| | | | | $C_{15}H_{23}NO_4$ | M. Wt. = 281 | | |
| 95 | $(CH_3)_2CHO(CH_2)_3-$ | R: petroleum ether/ether | 42–43 | calc. 65.99 | 8.80 | 4.53 | 20.68 |
| | | | | found 66.2 | 8.7 | 4.5 | 20.7 |
| | | | | $C_{17}H_{27}NO_4$ | M. Wt. = 309 | | |
| 96 | $(CH_3O)_2CH-CH(CH_3)-$ | CC: 1:3 ethyl acetate/cyclohexane | oil | calc. 61.72 | 8.09 | 4.50 | 25.68 |
| | | | | found 61.5 | 7.8 | 4.4 | 25.8 |
| | | | | $C_{16}H_{25}NO_5$ | M. Wt. = 311 | | |
| 97 | 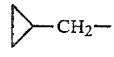–$CH_2-$ | R: ether/n-hexane | 66–67 | calc. 68.42 | 8.04 | 5.32 | 18.23 |
| | | | | found 68.3 | 7.7 | 5.3 | 18.6 |
| | | | | $C_{15}H_{21}NO_3$ | M. Wt. = 263 | | |
| 98 | 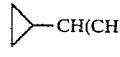–$CH(CH_3)-$ | R: cyclohexane | 72–73 | calc. 69.1 | 8.6 | 5.0 | 17.3 |
| | | | | found 69.5 | 8.5 | 5.0 | 17.3 |
| | | | | $C_{16}H_{23}NO_3$ | M. Wt. = 277 | | |
| 99 | 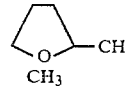–$CH_2-$ | R: ether | 44–45 | calc. 65.51 | 7.90 | 4.77 | 21.80 |
| | | | | found 65.3 | 7.7 | 4.8 | 21.8 |
| | | | | $C_{16}H_{23}NO_4$ | M. Wt. = 293 | | |
| 100 | 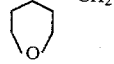 | R: hexane/ethyl acetate | 80–81 | calc. 67.27 | 8.47 | 4.36 | 19.90 |
| | | | | found 67.1 | 8.4 | 4.6 | 20.3 |
| | | | | $C_{18}H_{27}NO_4$ | M. Wt. = 321 | | |
| 101 | 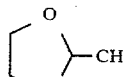 | CC: ethyl acetate/cyclohexane | oil | calc. 62.12 | 7.49 | 4.53 | 25.86 |
| | | | | found 61.9 | 7.5 | 4.5 | 26.0 |
| | | | | $C_{16}H_{23}NO_5$ | M. Wt. = 309 | | |

-continued

| Example No. | R¹ | Purification of the crude product | m.p. [°C.] | Analysis C | H | N | O |
|---|---|---|---|---|---|---|---|
| 102 | CH₃-CH(-O-CH₂-)(-O-CH-)-CH(CH₃)₂ (acetal structure) | CC: 1:3 ethyl acetate/cyclohexane | oil | calc. 66.46<br>found 66.7<br>$C_{21}H_{33}NO_5$ | 8.77<br>8.7 | 3.69<br>3.7<br>M. Wt. = 351.4 | 21.08<br>21.2 |
| 103 | $C_6H_5CH_2-$ | R: ether | 56–57 | calc. 72.2<br>found 72.1<br>$C_{18}H_{21}NO_3$ | 7.1<br>7.2 | 4.7<br>4.8<br>M. Wt. = 299 | 16.0 |
| 104 | furfuryl-CH₂— | R: ether | 70–71 | calc. 66.4<br>found 66.3<br>$C_{16}H_{19}NO_4$ | 6.6<br>6.6 | 4.8<br>4.9<br>M. Wt. = 289 | 22.2 |
| 105 | thienyl-CH₂— | R: ether | 60–61 | calc. 62.93<br>found 63.3<br>$C_{16}H_{19}NO_3S$ | 6.27<br>6.2 | 4.59<br>4.7<br>M. Wt. = 305 | 15.72<br>16.1 (S 10.50) |
| 106 | $C_6H_5-CH(CH_3)-CH_2-$ | CC: 3:7 ethyl acetate/cyclohexane | oil | calc. 73.4<br>found 72.8<br>$C_{20}H_{25}NO_3$ | 7.7<br>7.6 | 4.3<br>4.2<br>M. Wt. = 327 | 14.7 |
| 107 | 3,4-(CH₃O)₂-C₆H₃-CH₂-CH₂— | R: ether/ethyl acetate | 82–83 | calc. 67.5<br>found 67.4<br>$C_{21}H_{27}NO_5$ | 7.2<br>7.1 | 3.8<br>3.6<br>M. Wt. = 373 | 21.5 |
| 108 | $(C_6H_5)_2CH-CH_2CH_2-$ | CC: 2:5 ethyl acetate/cyclohexane | 80–81 | calc. 77.39<br>found 77.2<br>$C_{26}H_{29}NO_3$ | 7.24<br>7.4 | 3.47<br>3.6<br>M. Wt. = 403 | 11.89<br>12.1 |
| 109 | cyclopropyl | R: cyclohexane/ethyl acetate | 57–58 | calc. 67.4<br>found 67.6<br>$C_{14}H_{19}NO_3$ | 7.7<br>7.6 | 5.6<br>5.6<br>M. Wt. = 249 | 19.3 |
| 110 | cyclobutyl | R: cyclohexane | 70–71 | calc. 68.42<br>found 68.6<br>$C_{15}H_{21}NO_3$ | 8.04<br>8.0 | 5.32<br>5.3<br>M. Wt. = 263 | 18.23<br>18.2 |
| 111 | cyclopentyl | R: ethyl acetate | 98–99 | identical with substance from Example 15 | | | |
| 112 | cyclohexyl | R: ethyl acetate | 108–109 | calc. 70.1<br>found 69.8<br>$C_{17}H_{25}NO_3$ | 8.6<br>8.3 | 4.8<br>4.5<br>M. Wt. = 291 | 16.5 |
| 113 | 3,3,5-trimethylcyclohexyl | R: ether | 104–105 | calc. 72.04<br>found 71.9<br>$C_{20}H_{31}NO_3$ | 9.37<br>9.4 | 4.20<br>4.3<br>M. Wt. = 333 | 14.39<br>14.5 |
| 114 | 4-methylcyclohexyl | R: ether | 115–116 | calc. 70.79<br>found 70.8<br>$C_{18}H_{27}NO_3$ | 8.91<br>8.7 | 4.59<br>4.6<br>M. Wt. = 305 | 15.72<br>16.0 |
| 115 | cyclobutyl-CH₂— | CC: 1:5 ethyl acetate/cyclohexane | 75–76 | calc. 69.29<br>found 69.2<br>$C_{16}H_{23}NO_3$ | 8.36<br>8.1 | 5.05<br>4.7<br>M. Wt. = 277 | 17.30<br>18.2 |
| 116 | cyclopentyl-CH₂— | R: ethyl acetate | 78–80 | calc. 70.07<br>found 69.9<br>$C_{17}H_{25}NO_3$ | 8.65<br>8.7 | 4.81<br>5.6<br>M. Wt. = 291 | 16.47<br>16.2 |
| 117 | cyclohexyl-CH₂— | CC: 1:7 ethyl acetate/cyclohexane | 78–80 | calc. 70.79<br>found 70.4<br>$C_{18}H_{27}NO_3$ | 8.91<br>8.5 | 4.58<br>4.5<br>M. Wt. = 305 | 15.72<br>16.0 |
| 118 | cyclohexyl-CH(CH₃)— | CC: 1:7 ethyl acetate/cyclohexane | 94–96 | calc. 71.44<br>found 71.4<br>$C_{19}H_{29}NO_3$ | 9.15<br>8.9 | 4.38<br>3.8<br>M. Wt. = 319 | 15.03<br>15.4 |

Examples 119 to 126. Reaction of (1-acetylcyclohex-3-enyl)-methyl phenyl carbonate (Example XX) with an amine R¹NH₂

| Example No. | R¹ | Purification of the crude product | m.p. [°C.] | Analysis C | H | N | O |
|---|---|---|---|---|---|---|---|
| 119 | n-C₃H₇ | CC: 3:7 ethyl acetate/cyclohexane | oil | identical with substance from Example 52 | | | |
| 120 | n-C₄H₉ | CC: 2:3 ethyl acetate/cyclohexane | oil | identical with substance from Example 53 | | | |
| 121 | n-C₅H₁₁ | CC: 1:5 ethyl acetate/cyclohexane | oil | calc. 67.38<br>found 66.9<br>$C_{15}H_{25}NO_3$ | 9.42<br>9.4 | 5.24<br>5.3<br>M. Wt. = 267 | 17.95<br>18.4 |
| 122 | n-C₆H₁₃ | CC: 1:5 ethyl acetate/cyclohexane | oil | calc. 68.29<br>found 67.9<br>$C_{16}H_{27}NO_3$ | 9.67<br>9.5 | 4.98<br>5.0<br>M. Wt. = 281 | 17.06<br>16.9 |
| 123 | i-C₃H₇ | CC: 1:1 ethyl ace- | oil | identical with substance from Example 54 | | | |

-continued

| Example No. | R¹ | Purification of the crude product | m.p. [°C.] | Analysis | | | |
|---|---|---|---|---|---|---|---|
| | | | | | C | H | N | O |
| 124 | CH$_3$—CH$_2$—CH(CH$_3$)— | CC: 1:5 ethyl acetate/cyclohexane | 45–46 | calc. found | 66.37 66.6 C$_{14}$H$_{23}$NO$_3$ | 9.15 8.8 | 5.53 5.3 M. Wt. = 253 | 18.95 19.1 |
| 125 | ▷—CH(CH$_3$)— | CC: 1:7 ethyl acetate/cyclohexane | 73–75 | calc. found | 67.92 67.0 C$_{15}$H$_{23}$NO$_3$ | 8.68 8.5 | 5.28 5.0 M. Wt. = 265 | 18.11 18.8 |
| 126 | ▷— | CC: 1:5 ethyl acetate/cyclohexane | oil | calc. found | 65.80 65.8 C$_{13}$H$_{19}$NO$_3$ | 8.07 8.1 | 5.90 5.7 M. Wt. = 237.3 | 20.23 20.8 |

EXAMPLE 127

2-(N-Cyclopentylcarbamyloxymethyl)-bicyclo[2.2.2]oct-5-en-2-yl methyl ketone

Following the general method described, (2-acetyl-bicyclo[2.2.2]oct-5-ene-2-yl)-methyl phenyl carbonate (Example XIX) is reacted with cyclopentylamine to give 2-(N-cyclopentylcarbamyloxymethyl)-bicyclo[2.2.2]oct-5-en-2-yl methyl ketone. The crude product is recrystallized from ether. Melting point 77°–78° C.

Analysis calc. 70.07%, 8.65% H, 4.81%, 16.47% O: found 70.2% C, 8.6% H, 5.0% N, 16.5% O: C$_{17}$H$_{25}$NO$_3$ M.Wt.=291.

EXAMPLE 128

2-(N-Cyclopentylcarbamyloxymethyl)-bicyclo[2.2.2]oct-2-yl methyl ketone

Using the general method described, cyclopentylamine and (2acetylbicyclo[2.2.2]oct-2-yl)-methyl phenyl carbonate (Example XXI) give 2-(N-cyclopentylcarbamyloxymethyl)-bicyclo[2.2.2]oct-2-yl methyl ketone, melting, after recrystallization from ether, at 111°–112° C. (identical with the substance from Example 49).

C. EXAMPLES 129 to 133

General method for hydrogenating the ring double bond of carbamates of the formula I A solution of 50 millimoles of an unsaturated carbamate of the formula I, in 50 ml of methanol, is hydrogenated at room temperature, in the presence of 0.1-1 g of 10% strength palladium on charcoal, until the theoretical amount of hydrogen has been absorbed or until the hydrogen absorption ceases. After filtering off the catalyst, the solvent is distilled off under reduced pressure and the residue is recrystallized or purified by column chromatography. Saturated carbamates of the formula I are obtained in 60–95% yield.

The compounds of Examples 129 to 133 (formula I, R$^2$=CH$_3$; R$^3$ and R$^4$=H) are prepared by this method.

| Example No. | Starting substance Example No. | A,A | R¹ | Purification | m.p. [°C.] | Identical with substance from Example |
|---|---|---|---|---|---|---|
| 129 | 7 | —CH$_2$— | i-C$_3$H$_7$ | CC: 1:3 ethyl acetate/cyclohexane | 79–80 | 36 |
| 130 | 41 | —CH$_2$—CH$_2$— | C$_2$H$_5$ | R: ethyl acetate/petroleum ether | 60–61 | 46 |
| 131 | 42 | —CH$_2$—CH$_2$— | n-C$_3$H$_7$ | R: ether/n-hexane | 55–56 | 47 |
| 132 | 54 | H,H | i-C$_3$H$_7$ | CC: 1:1 ethyl acetate/cyclohexane | 46–47 | 71 |
| 133 | 53 | H,H | n-C$_4$H$_9$ | CC: 1:1 ethyl acetate/cyclohexane | oil | 70 |

EXAMPLE 134

2-[N-(4-Methoxy-3-methylphenyl)-carbamyloxymethyl]-norborn-5-en-2-yl methyl ketone 2.1 g of 80% strength NaH suspension are added to a solution of 10.54 g (0.77 mole) of 4-methoxy-3-methylaniline in 30 ml of THF and the mixture is heated to 40° C. to complete the elimination of hydrogen. When this has ceased, a solution of 20.0 g (0.77 mole) of (2-acetylnorborn-5-en-2-yl)-methyl phenyl carbonate in 20 ml of tetrahydrofuran is added dropwise at room temperature, and the mixture is then stirred for 18 hours at 20° C.

After having added a small amount of water, the solvent is stripped off and the residue is taken up in ether. The ether phase is washed repeatedly with 5% strength sodium hydroxide solution, and with water, and is dried over sodium sulfate. The crystalline crude product (11.8 g) is recrystallized from ethyl acetate; 6.4 g of 2-[N-(4-methoxy-3-methylphenyl)-carbamyloxymethyl]-norborn-5-en-2-yl methyl ketone, of melting point 121°–122° C., are obtained.

Analysis calc. 69.28% C, 7.04% H, 4.25% N, 19.4% O: found 69.4% C, 6.9% H, 4.3% N: C$_{19}$H$_{23}$NO$_4$ $M.Wt.$=329.

EXAMPLES 135 to 137

General method for reacting (2-acetylnorborn-5-en-2-yl)-methyl phenyl carbonate with an amine hydrochloride (the amine being liberated in situ).

0.023 mole of amine hydrohalide (R$^1$NH$_2$.HX, X=Cl or Br) are first added, at 20° C., to a solution of 6.0 g (0.021 mole) of (2-acetylnorborn-5-en-2-yl)-methyl phenyl carbonate in 30 ml of absolute methanol, and a solution of 1.1 g (0.021 mole) of sodium methylate in 20 ml of methanol is then added dropwise over 2 hours. Thereafter the reaction is allowed to continue for 15-60 minutes at room temperature, and the solvent is then stripped off under reduced pressure. The residue is diluted with water and repeatedly extracted with ether. The combined organic phases are then extracted by shaking three times with 5% strength sodium hydroxide solution and once with water, and are dried over sodium sulfate and concentrated on a rotary evaporator; the product is then chromatographed on a silica gel column.

The yield of pure product is from 30 to 50%, based on (2-acetylnorborn-5-en-2-yl)-methyl phenyl carbonate employed. It can be increased to above 50% by using from 2 to 4 equivalents of amine hydrohalide and sodium methylate per equivalent of carbonate.

(N-cyclopropylcarbamyloxymethyl)-norborn-5-en-2-yl methyl ketone, exo-2-(N-(2-methylpropyl)-carbamyloxymethyl)-norborn-5-en-2-yl methyl ketone, exo-2-(N-but-2-ylcarbamyloxymethyl)-norborn-5-en-2-yl methyl ketone, 1-(N-propylcarbamyloxymethyl)-cyclohex-3-en-yl methyl ketone and exo-2-[N-(1-cyclopropylethyl)-carbamyloxymethyl]-norborn-5-en-2-yl methyl ketone.

EXAMPLE 139

40 g of a mixture of norbornenyl methyl ketone and 2-hydroxymethylnorborn-5-en-2-yl methyl ketone (exo: endo ratio about 2:8), in 64 ml of tetrahydrofuran, are reacted with 22.4 g of isopropyl isocyanate in the presence of 0.4 g of dibutyl-tin diacetate. When the exothermic reaction (which raises the temperature to 50° C.) has subsided, the mixture is stirred for 3 hours at room Examples 135 to 137:

| Example No. | $R^1$ | Purification of the crude product | m.p. [°C.] | Analysis | | | | |
|---|---|---|---|---|---|---|---|---|
| | | | | | C | H | N | O | Hal |
| 135 | $ClCH_2CH_2$— | CC: 1:4 ethyl acetate/cyclohexane | 74-75 | calc. found $C_{13}H_{18}ClNO_3$ | 57.46 57.6 | 6.68 6.7 | 5.15 5.0 M. Wt. | 17.66 17.5 = 272 | Cl 13.05 Cl 13.0 |
| 136 | Cl—$CH_2$—$CH_2$—$CH_2$— | CC: 1:4 ethyl acetate/cyclohexane | 41-43 | calc. found $C_{14}H_{20}ClNO_3$ | 58.84 59.0 | 7.05 7.1 | 4.90 4.7 M. Wt. | 16.80 17.0 = 286 | Cl 12.41 Cl 12.4 |
| 137 | Br—$CH_2$—$CH_2$—$CH_2$— | CC: 3:7 ethyl acetate/methylene chloride | Oil | calc. found $C_{14}H_{20}BrNO_3$ | 50.92 51.0 | 6.10 6.1 | 4.24 4.3 M. Wt. | 14.54 15.5 = 330 | Br 24.20 Br 23.7 |

EXAMPLE 138

1-(N-Isopropylcarbamyloxymethyl)-cyclohex-3-enyl methyl ketone

A solution of 10.0 g of 1-hydroxymethylcyclohex-3-enyl methyl ketone (Example IX) in 10 ml of ether is added dropwise to a solution of 12.5 g of phosgene in 60 ml of absolute ether at +5° C. After stirring the mixture for three hours at room temperature, the excess phosgene and the solvent are distilled off on a rotary evaporator and the residue [(1-acetylcyclohex-3-enyl)-methyl chlorocarbonate] is taken up in 100 ml of absolute toluene. 17.7 g of isopropylamine are added, whereupon the temperature rises to +40° C.; the mixture is then stirred for 3 hours at 80° C., cooled to room temperature and poured into 150 ml of water. After separating off the organic phase, the aqueous phase is twice extracted with toluene. The combined toluene phases are washed once with water and are dried over sodium sulfate. After distilling off the solvent, the crude product is purified by column chromatography (eluant: a 1:4 ethyl acetate/cyclohexane mixture). 10.7 g of 1-(N-isopropyl-carbamyloxymethyl)-cyclohex-3-enyl methyl ketone, which is pure according to NMR spectroscopy, and is identical with the prdouct from Example 54, are obtained. In addition, 1.8 g of the keto-alcohol (Example IX) are recovered. The yield, based on unrecovered keto-alcohol, is 84%.

Using a similar method, the following are obtained, in similar yields, from the corresponding chlorocarbonic acid esters of the formula IV, which are prepared in situ from a keto-alcohol of the formula II (Example XIII, IX and XV) and phosgene: exo-2-(N-isopropylcarbamyloxymethyl)-norborn-5-en-2-yl methyl ketone, exo-2-(N-n-propylcarbamyloxymethyl)-norborn-5-en-2-yl methyl ketone, exo-2-(N-cyclopentylcarbamyloxymethyl)-norborn-5-en-2-yl methyl ketone, exo-2-(N-isopropylcarbamyloxymethyl)-norborn-2-yl methyl ketone, exo-2- temperature, and the solvent is then distilled off. 65 g of a yellow oil, which substantially crystallizes, are obtained. After recrystallization from a 1:1 cyclohexane/hexane mixture, 35.5 g of 2-(N-isopropylcarbamyloxymethyl)-norborn-5-en-2-yl methyl ketone, of melting point 78°-79° C., are obtained. Further recrystallization gives 26.4 g of exo-2-(N-isopropylcarbamyloxymethyl)-norborn-5-en-2-yl methyl ketone of melting point 84° C.

D. Examples of formulations prepared in a conventional manner:

| 1. | Tablets | |
|---|---|---|
| (a) | Active compound of the formula I | 50 mg |
| | Lactose | 200 mg |
| | Methylcellulose | 15 mg |
| | Corn starch | 50 mg |
| | Talc | 11 mg |
| | Magnesium stearate | 4 mg |
| | | 330 mg |
| (b) | Active compound of the formula I | 20 mg |
| | Lactose | 178 mg |
| | ®Avicel (microcrystalline cellulose) | 80 mg |
| | Polywachs 6000 (polyethylene glycol, mean M. Wt. 600) | 20 mg |
| | Magnesium stearate | 2 mg |
| | | 300 mg |
| (c) | Active compound of the formula I | 250 mg |
| | Polyvinylpyrrolidone (mean molecular weight, 25,000) | 170 mg |
| | Polyethylene glycol (mean molecular weight, 4,000) | 14 mg |
| | Hydroxypropylmethylcellulose | 40 mg |
| | Talc | 4 mg |
| | Magnesium stearate | 2 mg |
| | | 480 mg |

Formulation (c) may be obtained by the following steps: The active compound is moistened with a 10% strength aqueous solution of the polyvinylpyrrolidone and the mixture is forced through a sieve of 1.0 mm mesh width and is dried at 50° C. The granules obtained are mixed with polyethylene glycol (mean molecular weight 4000), hydroxypropylmethylcellulose, talc and magnesium stearate, and the mixture is pressed to form tablets each weighing 280 mg.

| 2. | Dragees | |
|---|---|---|
| | Compound of the formula I | 50 mg |
| | Lactose | 90 mg |
| | Corn starch | 60 mg |
| | Polyvinylpyrrolidone | 6 mg |
| | Magnesium stearate | 1 mg |
| | | 207 mg |

The mixture of active compound, lactose and corn starch is moistened with an 8% strength aqueous solution of the polyvinylpyrrolidone and forced through a 1.5 mm sieve, and the granules obtained are dried at 50° C. and forced through a 1.0 mm sieve. The granules obtained after this stage are mixed with magnesium stearate and the mixture is pressed to form dragee cores. The cores obtained are provided, in a conventional manner, with a coating consisting essentially of sugar and talc.

| 3. | Capsules | |
|---|---|---|
| | Active compound of the formula I | 50 mg |
| | Magnesium stearate | 2 mg |
| | Lactose | 30 mg |
| | | 82 mg |
| 4. | Injection solution | |
| | Active compound of the formula I | 100 mg |
| | Sodium chloride | 9 mg |
| | Distilled water, to make up to 10 ml. | |

We claim:

1. A compound of the formula I

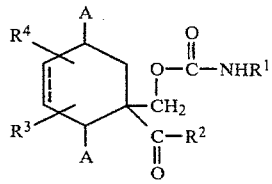

where the broken line is a double bond which may or may not be hydrogenated and the radicals A are each hydrogen, or the two radicals A together are a bridge, joining the two carbon atoms, of the formula $—(CH_2)_m—$, where m is an integer from 1 to 3, and which may or may not be substituted by 1, 2 or 3 lower alkyl, or a bridge of the formula

where n is an integer from 2 to 4, and $R^1$ is hydrogen, or is a saturated straight-chain or branched alkyl radical of 1 to 12 carbon atoms, which is unsubstituted, or is monosubstituted, disubstituted or trisubstituted by halogen, lower alkoxy or lower alkylthio, or is monosubstituted by cyano or by cycloalkyl of 3 to 6 carbon atoms in the ring, which ring is unsubstituted or substituted by 1, 2 or 3 lower alkyl and may, in the case of a 5-membered or 6-membered ring, have 1 or 2 carbon atoms replaced by oxygen or sulfur, or by bicycloalkyl of 5 to 8 carbon atoms in the bicyclic system, which is unsubstituted or substituted by 1, 2 or 3 lower alkyl, or is monosubstituted or disubstituted by phenyl, furyl or thienyl, which are unsubstituted or substituted by halogen, lower alkyl or lower alkoxy, or is alkenyl or alkynyl of 2 to 12 carbon atoms, alkenyl being unsubstituted or substituted by 1, 2 or 3 chlorine atoms, or is cycloalkyl of 3 to 7 carbon atoms in the ring, which ring is unsubstituted or substituted by 1, 2, 3 or 4 lower alkyl or by phenyl and may, in the case of a 5-membered or 6-membered ring, have 1 or 2 carbon atoms replaced by oxygen or sulfur, or is bicycloalkyl of 5 to 8 carbon atoms in the bicyclic system, which is saturated or unsaturated and is unsubstituted or substituted by 1, 2 or 3 lower alkyl, or is phenyl, furyl or thienyl, which is unsubstituted or monosubstituted or disubstituted by halogen, lower alkyl or lower alkoxy, $R^2$ is saturated straight-chain or branched alkyl of 1 to 6 carbon atoms and $R^3$ and $R^4$ independently of one another are each hydrogen or lower alkyl.

2. A compound of the formula I as claimed in claim 1, where the broken line is a double bond, which may or may not be hydrogenated, the radicals A are hydrogen or together form a bridge of the formula $—(CH_2)_m—$, where m is 1 or 2, and $R^1$ is saturated straight-chain or branched alkyl of 1 to 6 carbon atoms, which is unsubstituted, or is monosubstituted, disubstituted or trisubstituted by halogen, or is monosubstituted by lower alkoxy, by cyano, by lower alkylthio, by cycloalkyl of 3 to 6 carbon atoms in the ring, which is unsubstituted or substituted by lower alkyl and, in the case of a 5-membered or 6-membered ring, may contain an oxygen or a sulfur in place of 1 carbon atom or of 2 non-adjacent carbon atoms, or by furyl, or is alkenyl or alkynyl of 2 to 6 carbon atoms, alkenyl being unsubstituted or substituted by 1, 2 or 3 chlorine atoms, or is cycloalkyl of 3 to 6 carbon atoms in the ring, which is unsubstituted or substituted by 1, 2 or 3 lower alkyl, $R^2$ is methyl or ethyl and $R^3$ and $R^4$ are each hydrogen or methyl.

3. A compound of the formula I as claimed in claim 1, where the broken line is a double bond, which may or may not be hydrogenated, and the radicals A are each hydrogen or together are methylene, and $R^1$ is saturated, straight-chain or branched unsubstituted alkyl of 1 to 6 carbon atoms, or alkyl of 1 to 3 carbon atoms which is substituted by chlorine, by lower alkoxy of 1 to 3 carbon atoms, or by cycloalkyl of 3 or 4 carbon atoms, or is alkenyl or alkynyl of 2 to 6 carbon atoms or is cycloalkyl of 3 to 5 carbon atoms in the ring, $R^2$ is methyl and $R^3$ and $R^4$ are each hydrogen.

4. Exo-2-(N-Isopropylcarbamyloxymethyl)-norborn-5-en-2-yl methyl ketone.

5. Exo-2-(N-n-Propylcarbamyloxymethyl)-norborn-5-en-2-yl methyl ketone.

6. Exo-2-(N-Cyclopentylcarbamyloxymethyl)-norborn-5-en-2-yl methyl ketone.

7. Exo-2-(N-Isopropylcarbamyloxymethyl)-norborn-2-yl methyl ketone.

8. Exo-2-(N-Cyclopropylcarbamyloxymethyl)-norborn-5-en-2-yl methyl ketone.

9. Exo-2-[N-(2-Methylprop-1-yl)-carbamyloxymethyl]-norborn-5-en-2-yl methyl ketone.

10. Exo-2-(N-But-2-ylcarbamyloxymethyl)-norborn-5-en-2-yl methyl ketone.

11. 1-(N-Propylcarbamyloxymethyl)-cyclohex-3-enyl methyl ketone.

12. Exo-2-[N-(1-Cyclopropylethyl)-carbamyloxymethyl]-norborn-5-en-2-yl methyl ketone.

13. A hypnotic or sedative composition containing a hypnotic or sedative effective amount of a compound of the formula I as claimed in claim 1, as the active compound, together with conventional carriers and diluents.

14. A method of treating sleep disturbance comprising administering to a host in need thereof a hypnotic effective amount of a compound of the formula (I), as claimed in claim 1.

15. A method of treating sleep disturbance comprising administering to a host in need thereof a sedative effective amount of a compound of the formula (I), as claimed in claim 1.

* * * * *